United States Patent [19]

Nakatani et al.

[11] Patent Number: 4,570,005
[45] Date of Patent: Feb. 11, 1986

[54] PROCESS FOR THE PREPARATION OF 2-ARYLPROPYL ETHER OR THIOETHER DERIVATIVES

[75] Inventors: Kiyoshi Nakatani, Tokyo; Satoshi Numata, Kanagawa; Tsuneo Inoue, Kanagawa; Kenji Kodaka, Kanagawa; Tsutomu Ishii, Kanagawa; Teruhiko Toyama, Kanagawa; Hajime Tachibana, Kanagawa; Takatoshi Udagawa, Kanagawa; Masatoshi Gohbara, Kanagawa, all of Japan

[73] Assignee: Mitsuitoatsu Chemicals Inc., Tokyo, Japan

[21] Appl. No.: 513,930

[22] Filed: Jul. 14, 1983

Related U.S. Application Data

[62] Division of Ser. No. 254,135, Apr. 14, 1981, Pat. No. 4,397,864.

[30] Foreign Application Priority Data

May 2, 1980 [JP] Japan ................... 55-057872
Oct. 24, 1980 [JP] Japan ................... 55-148279

[51] Int. Cl.[4] .................. C07D 307/42; C07D 307/38
[52] U.S. Cl. ......................... 549/435; 549/445;
549/497; 260/465 F; 560/18; 560/64; 568/39;
568/42; 568/52; 568/56; 568/57; 568/58;
568/331; 568/333; 568/632; 568/633; 568/636;
568/637; 568/640
[58] Field of Search .............. 549/497, 435, 445;
568/632, 633, 636, 637, 640, 39, 56, 52, 42, 57,
58, 333, 331; 260/465 F; 560/18, 64

[56] References Cited

PUBLICATIONS

Winstein, S., et al, "Neighboring Carbon and Hydrogen. V. Driving Forces in the Wagner-Meerwein Rearrangement", *J. Am. Chem. Soc.*, vol. 74, No. 5, pp. 1113–1120, (1952).
Heck, R., et al, "Neighboring Carbon and Hydrogen. XXIX. p-o Analysis of Acetolysis of Substituted Neophyl Arylsulfonates" *J. Am. Chem. Soc.*, vol. 79, No. 13, 3432–3438 (1957).
Wagner et al., Synthetic Organic Chemistry, John Wiley, pp. 787–788.
Cram, D. J., et al, *Organic Chemistry*, pp. 200–209, McGraw-Hill, (1959).
W. H. Saunders, Jr. et al, "Phenyl vs. Methyl Migration Aptitudes in Some Carbonium Ion Reactions of Neophyl Derivatives", *J. Am. Chem. Soc.*, vol. 83, No. 4, pp. 882–885 (1961).
Fainberg, A. H. et al, "Salt Effects on Ion Pairs in Solvolysis and Related Reactions", *J. Am. Chem. Soc.*, vol. 78, No. 12, pp. 2763–2767 (1956).

Primary Examiner—Henry R. Jiles
Assistant Examiner—Bernard I. Dentz
Attorney, Agent, or Firm—Browdy and Neimark

[57] ABSTRACT

2-Arylpropyl ether or thioether derivatives represented by the following general formula [I]:

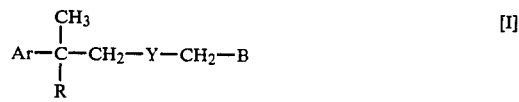

wherein Ar stands for an aryl group, R stands for a methyl or ethyl group, Y stands for an oxygen or sulfur atom, and B stands for a group represented by the following formula [II]:

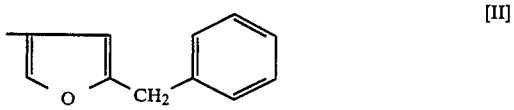

or the following general formula [III]:

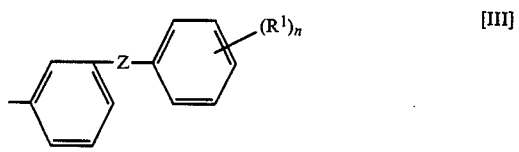

wherein Z stands for an oxygen or sulfur atom or a carbonyl or methylene group, $R^1$ stands for a hydrogen or halogen atom or a lower alkyl group or a lower alkoxy group, and n is an integer of from 1 to 5 with the proviso that when n is 2 or more, the groups $R^1$ may be the same or different, are produced by reacting a compound represented by the following formula (V):

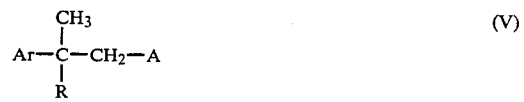

with a compound represented by the following formula (VI):

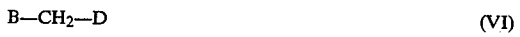

wherein Ar, R and B are defined above, A is a halogen atom and D is Y—H in which Y is as defined above, in the presence of a base in dimethylsulfoxide or sulfolane. The compounds thus prepared have excellent insecticidal and acaricidal activities while the toxicity of these compounds are very low.

1 Claim, No Drawings

PROCESS FOR THE PREPARATION OF 2-ARYLPROPYL ETHER OR THIOETHER DERIVATIVES

This is a division of application Ser. No. 254,135 filed Apr. 14, 1981 now U.S. Pat. No. 4,397,864.

DETAILED DESCRIPTION OF THE INVENTION

The present invention relates to novel 2-arylpropyl ether or thioether derivatives, processes for the preparation thereof, insecticidal and acaricidal agents containing these novel compounds, and an insecticidal and acaricidal method using these novel compounds.

More specifically, in accordance with one aspect of the present invention, there are provided 2-arylpropyl ether or thioether derivatives represented by the following general formula [I]:

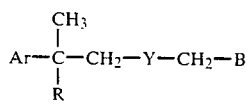   [I]

wherein Ar stands for an aryl group, R stands for a methyl or ethyl group, Y stands for an oxygen or sulfur atom, and B stands for a group represented by the following formula [II]:

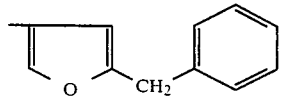   [II]

or the following general formula [III]:

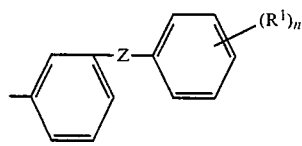   [III]

wherein Z stands for an oxygen or sulfur atom or a carbonyl or methylene group, $R^1$ stands for a hydrogen or halogen atom or a lower alkyl group or a lower alkoxy group, and n is an integer of from 1 to 5 with the proviso that when n is 2 or more, the groups $R^1$ may be the same or different.

In accordance with another aspect of the present invention, there are provided processes for the preparation of 2-arylpropyl ether or thioether derivatives represented by the above general formula [I], which comprises reacting a compound represented by the following general formula [V]:

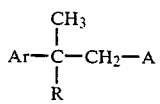   [V]

with a compound represented by the following general formula [VI]:

B—CH$_2$—D   [VI]

wherein Ar, R and B are as defined above, and one of groups A and D stands for a halogen atom and the other group is a group Y—M in which Y is as defined above and M stands for a hydrogen atom or an alkali metal or alkaline earth metal atom or both A and D stand for a hydroxyl group.

In accordance with still another aspect of the present invention, there are provided insecticidal and acaricidal agents comprising 2-arylpropyl ethers represented by the above general formula [I] and/or 2-arylpropyl thioethers represented by the above general formula [I].

In accordance with still another aspect of the present invention, there is provided an insecticidal and acaricidal method using 2-arylpropyl ether derivatives represented by the above general formula [I] and/or 2-arylpropyl thioether derivatives represented by the above general formula [I].

Insecticides have taken very important roles in improving productivities in various fields of agriculture. Development of organic synthetic agricultural chemicals changed completely the food situation for man, and agricultural chemicals have made great contributions to prevention of infectious diseases through the medium of insect pests.

However, uses of organochlorine insecticides represented by DDT and BHC are now limited because they are left in applied environments for a long time after application. Organophosphorous insecticides and carbamate insecticides developed as substitutes for these organochlorine insecticides are now used widely in various fields, but a variety of insect pests having acquired resistances to these chemicals have already appeared and insect pests which can hardly be controlled grow in certain territories. The problem of control of chemical-resistant insect pests will expand and become serious.

For the purpose of maintaining the developing civilization of the mankind established up to the present, it is important to continuously supply foods sufficiently and stably, and in order to attain this object, it is eagerly desired to develop chemicals having an excellent insecticidal activity.

Under such background, synthetic pyrethroid insecticides have attracted attention, because they have an excellent insecticidal activity and are very effective for controlling insect pests having acquired resistances to organophosphorous insecticides or carbamate insecticides while they have low toxicity to men and animals. However, these synthetic pyrethroid insecticides have a fatal defect in that the fish toxicity is very high, and the application ranges of these chemicals are strictly limited because of this fatal defect. Moreover, these synthetic pyrethroid insecticides are much more expensive than other synthetic insecticides heretofore developed.

These defects should be eliminated in agricultural chemicals which will be developed for the future. More specifically, it is desired to develop insecticides which have a high safety, are readily decomposed without being left in applied environments, hence do not cause any environmental pollution, have a high activity of controlling insect pests having acquired a resistance to insecticides and are manufactured at low cost.

Research has been made with a view to developing insecticidal and acaricidal agents satisfying the foregoing requirements, and it has been found that specific 2-arylpropyl ether or thioether derivatives have high insecticidal and acaricidal activities, are excellent in their fast-acting property and residual activity, are of lowtoxicity to not only men and animals but also fish and can be supplied at a relatively low cost.

The present research has continued for obtaining active compounds and also for confirming insecticidal and acaricidal characteristics of these compounds, and it was found that according to an appropriate combination of two alcohol residues in the abovementioned ether or thioether derivatives, these compounds can posses selective and non-selective activities to insect pests belonging to orders of Coleoptera, Lepidoptera, Orthoptera, Hemiptera, Isoptera and Acarina and these compounds have a broad insecticidal spectrum and that very excellent insecticidal compositions having a very low toxicity to men and animals can be prepared from these compounds. It also was found that most of these compounds are very low in their toxicity to fish.

The present invention has now been completed based on these findings.

The compounds of the present invention have an active structure quite different from those of the conventional agricultural chemicals. They have an excellent insecticidal activity to sanitary insect pests such as fly, mosquito and cockroach and agricultural insect pests such as planthoppers, leafhoppers, worms, moths, leaf holders, aphids, borers and mites, especially green rice leafhopper, and furthermore, they are effective for controlling stored grain insect pests such as grain mite, Indian meal moth and rice weevil, animal-parasitic mites and lice, and other insect pests. Furthermore, the compounds of the present invention are excellent in the fast-acting property and residual activity and have a flushing effect. Moreover, the compounds of the present invention have not only a knock-down effect to kill insect pests but also a repellent action of insect pests from hosts. Still further, the compounds of the present invention have submerged application effects and are advantageous in that the phyto-toxicity to plants of Solanacede, which is observed in Fenvalerate, one of the typical instances of synthetic pyrethroids, is not observed at all. In addition, the compounds of the present invention are very low in their toxicity to mammals, and some of the compounds of the present invention have a high safety to fish and they are suitably applied for controlling insect pests in paddy fields and aquatic insect pests such as larvae of mosquitoes and gnats and also are used for aerial application over broad districts including lakes, marshes, ponds and rivers without a fear of extermination of fish.

Accordingly, insecticidal and acaricidal compositions comprising the compounds of the present invention can be applied very widely in various fields and have a very high controlling effect to agricultural and horticultural insect pests, stored grain insects, sanitary insect pests, household insect pests, forest insect pests and aquatic insect pests. Moreover they are very safe and can be supplied at low cost in the form of various formulations.

The 2-arylpropyl ether and thioether derivatives represented by the general formula [I] according to the present invention are novel compounds. The aryl group Ar includes aromatic hydrocarbon groups such as phenyl, naphthyl, anthryl and phenanthryl groups, which may be unsubstituted or substituted with the same or different substituents selected from the substituents described hereinafter. As the substituent, there can be mentioned, for example, a halogen atom, an alkyl group, a haloalkyl group, a phenyl group, an alkoxy group, a haloalkoxy group, a cycloalkoxy group, a phenoxy group, an alkenyl group, a haloalkenyl group, an alkynyl group, a haloalkynyl group, an alkoxyalkyl group, an alkenyloxy group, a haloalkenyloxy group, an alkynyloxy group, a haloalkynyloxy group, an alkylthio group, a haloalkylthio group, an alkylsulfinyl group, an acyl group, an alkoxyalkoxy group, an alkenylthio group, an alkoxycarbonyl group, a haloalkoxycarbonyl group, an alkynyloxycarbonyl group an alkenyloxycarbonyl group, a nitro group, a nitrile group, a haloalkenylthio group, a methylenedioxy group, a 3,4-difluoromethylenedioxy group, a 3,4-difluoroethylenedioxy group, a 3,4-trifluoroethylenedioxy group and a polymethylene group having 3 to 5 carbon atoms. Frowm the industrial viewpoint, unsubstituted aryl groups and mono- and poly-substituted aryl groups having same or different substituents selected from a halogen atom, a lower alkyl group, a lower haloalkyl group, a lower alkoxy group, a lower haloalkoxy group, a methylenedioxy group, a lower alkylthio group, a nitrile group and a nitro group are preferred.

Specific examples of the aryl group are mentioned below though aryl groups that can be used in the present invention are not limited to those exemplified below. As specific examples of the aryl group, there can be mentioned a phenyl group, a 4-methylphenyl group, a 3,4-dimethylphenyl group, a 4-trifluoromethylphenyl group, a 3-methylphenyl group, a 3-trifluoromethylphenyl group, a 4-chlorophenyl group, a 3,4-dichlorophenyl group, a 4-nitrophenyl group, a 4-methylthiophenyl group, a 4-methoxyphenyl group, a 3,4-dimethoxyphenyl group, a 3,4-methylenedioxyphenyl group, a 4-difluoromethylthiophenyl group, a 4-trifluoromethylthiophenyl group, a 3,4-difluoromethylenedioxyphenyl group, a 4-cyanophenyl group, a 4-fluorophenyl group, a 4-bromophenyl group, a 3,4-difluorophenyl group, a 3,4-dibromophenyl group, a 4-chloro-3-fluorophenyl group, a 3-chloro-4-fluorophenyl group, a 3-chloro-4-methylphenyl group, a 3-bromo-4-chlorophenyl group, a 4-difluoromethoxyphenyl group, a 3,4-bis(difluoromethoxy)phenyl group, a 4-trifluoromethoxyphenyl group, a 3,4-bis(trifluoromethoxy)phenyl group, a 4-methoxy-3,5-dimethylphenyl group, a 3,4-trifluoroethylenedioxyphenyl group, a 4-tert-butylphenyl group, a 4-ethylphenyl group, a 4-isopropylphenyl group, a 3,4-difluoroethylenedioxyphenyl group, a 4-isopropenylphenyl group, a 4-vinylphenyl group, a 4-(2,2-dichlorovinyl)phenyl group, a 4-chloro-3-methylphenyl group, a 3-bromo-4-fluorophenyl group, 2-naphthyl group, a 3-fluoro-4-bromophenyl group, a 4-fluoro-3-methylphenyl group, a 3-fluoro-4-methylphenyl group, a 3-bromo-4-methylphenyl group, a 3,4-diethylphenyl group, a 3,4-diisopropylphenyl group, a 3-ethyl-4-methylphenyl group, a 4-isopropyl-3-methylphenyl group, a 4-methoxymethoxyphenyl group, a 4-methylsulfinylphenyl group, a 4-allylphenyl group, a 4-acetylphenyl group, a 4-ethoxycarbonylphenyl group, a 4-ethoxyphenyl group, a 1,2,3,4-tetrahydronaphthalen-7-yl group, a 3,5-dichloro-4-methylphenyl group, an indan-5-yl group, a 4-propargylphenyl group, a 3-methoxy-4-methylphenyl group, a 4-methoxymethylphenyl group, a 4-(1-chloroethylen-1-yl)phenyl group, a 4-(2-chloroallyl)phenyl group, a 4-isobutyrylphenyl group, a 4-methoxycarbonylphenyl group, a 3-nitro-4,5-dimethylphenyl group, a 3-ethoxy-4-bromophenyl group, a 3-chloro-4-methoxyphenyl group, a 4-bromo-3-chlorophenyl group, a 3,4-(di-tert-butyl)phenyl group, a 4-ethyl-3-methylphenyl group, a 4-tert-butyl-3-methylphenyl group, a 4-(1,1,2,2-tetrafluoroethoxy)-phenyl group, a 4-(2,2-dichlorovinyloxy)phenyl group, a 4-(2,2,2-trifluoroethoxy)phenyl group, a 4-pentafluoroethoxyphenyl group, a 4-(chlorodifluoromethoxy)phenyl group, a 4-(chlorofluoromethoxy)-phenyl group, a 4-dichlorofluoromethoxy phenyl group, a 4-(1,1-difluoroethoxy)phenyl group, a 4-(1,2,2-trichloro-1,2-difluoroethoxy)phenyl group, a 4-(2-bromo-1,1,2,2-tetrafluoroethoxy)phenyl group, a 4-(2-propynyloxy)phenyl group, a 4-(1-propynyloxy)phenyl group, a 4-allyloxyphenyl group, a 4-ethynyloxyphenyl group, a 4-(2-chloroethynyl)phenyl group, a 4-(n-propoxy)phenyl group, a 4-(isopropoxy)phenyl group, a 4-cyclopentyloxyphenyl group, a 4-(n-pentyloxy)phenyl group, a 4-isobutoxy phenyl group, a 4-iodophenyl group, a 4-vinyloxyphenyl group, a 4-biphenyl group, a 4-(n-butoxy)phenyl group, a 4-(sec-butoxy)phenyl group, a 6-methyl-2-naphthyl group, a 4-phenoxyphenyl group, a 4-(2-iodo-1,1-difluoroethoxy)-phenyl group, a 4-cyclohexyloxyphenyl group, a 3-chloro-4-ethoxyphenyl group, a 4-ethoxymethoxyphenyl group, a 4-ethoxymethylphenyl group, a 4-ethoxyethoxyphenyl group, a 4-(1-ethoxyethyl)phenyl group, a 4-(1-methoxyethyl)phenyl group, a 4-ethoxy-3-methylphenyl group, a 4-(2-methyl-1-propenyl)phenyl group, a 4-(1,2,2-trichlorovinyloxy)phenyl group, a 3,4-diethoxyphenyl group, a 4-ethynylphenyl group, a 4-ethoxy-3,5-dimethylphenyl group, a 4-ethoxy-3-methoxyphenyl group, a 4-ethylthiophenyl group, a 4-(2,2,2-trifluoroethoxycarbonyl)phenyl group, a 4-(2-chloroethoxy)-phenyl group, a 4-(1-buten-2-yl)phenyl group and a 4-(2-buten-2-yl)phenyl group, a 4-vinylphenyl group.

As specific examples of the group B-CH$_2$-, there can be mentioned a 5-benzyl-3-furylmethyl group, a 3-phenoxybenzyl group, a 3-(4-fluorophenoxy)benzyl group, a 3-(4-bromophenoxy)benzyl group, a 3-(4-chlorophenoxy)benzyl group, a 3-(3-fluorophenoxy)benzyl group, a 3-(2-bromophenoxy)benzyl group, a 3-(3-chlorophenoxy)benzyl group, a 3-(4-methylphenoxy)benzyl group, a 3-(2-fluorophenoxy)-benzyl group, a 3-(2-chlorophenoxy)-benzyl group, a 3-(3-bromophenoxy)benzyl group, a 3-(3-methoxyphenoxy)-benzyl group, a 3-(2-methylphenoxy)benzyl group, a 3-(4-ethoxyphenoxy)benzyl group, a 3-(4-methoxyphenoxy)benzyl group, a 3-(3-methylphenoxy)benzyl group, a 3-(2-methoxyphenoxy)benzyl group, a 3-phenylthiobenzyl group, a 3-benzoylbenzyl group, a 3-benzylbenzyl group, a 3-(4-chlorobenzyl)benzyl group, a 3-(4-fluorobenzyl)-benzyl group, a 3-(3,5-dichlorophenoxy)benzyl group, a 3-(3,4-dichlorophenoxy)benzyl group, a 3-(4-chloro-2-methylphenoxy)benzyl group, a 3-(2-chloro-5-methylphenoxy)-benzyl group, a 3-(4-chloro-3-methylphenoxy)benzyl group, a 3-(4-ethylphenoxy)benzyl group, a 3-(3-chloro-5-methoxyphenoxy)benzyl group, a 3-(4-fluorophenylthio)benzyl group, a 3-(3-fluorophenylthio)benzyl group, a 3-(3,5-dichlorobenzoyl)benzyl group, a 3-(3,4-dichlorobenzoyl)benzyl group, a 3-(2,5-dichlorobenzoyl)benzyl group and a 3-(4-methylbenzyl)benzyl group.

Typical examples of the compounds according to the present invention will now be described. Of course, the compounds included in the scope of the present invention are not limited to those exemplified below.

Incidentally, in the case where R in the general formula [I] is an ethyl group, the compounds contain an asymmetric carbon atom and there are present optical isomers. These optical isomers and mixtures thereof are included in the scope of the present invention.

Examples of the compounds included in the scope of the present invention are as follows.
3-Phenoxybenzyl 2-(4-methoxyphenyl)-2-methyl propyl ether and thioether
3-(4-Fluorophenoxy)benzyl 2-(4-fluorophenyl)-2-ethylpropyl ether and thioether
3-Phenoxybenzyl 2-(4-methoxyphenyl)-2-ethylpropyl ether and thioether
3-(4-Fluorophenoxy)benzyl 2-(4-fluorophenyl)-2-methylpropyl ether and thioether
3-(4-Fluorophenoxy)benzyl 2-(4-methylphenyl)-2-methylpropyl ether and thioether
3-(4-Bromophenoxy)benzyl 2-(4-chlorophenyl)-2-methylpropyl ether and thioether
3-(4-Bromophenoxy)benzyl 2-(4-chlorophenyl)-2-ethylpropyl ether and thioether
3-Phenoxybenzyl 2-phenyl-2-methylpropyl ether and thioether
3-Phenoxybenzyl 2-phenyl-2-ethylpropyl ether and thioether
3-(4-Fluorophenoxy)benzyl 2-(4-chlorophenyl)-2-methylpropyl ether and thioether
3-(4-Fluorophenoxy)benzyl 2-(4-chlorophenyl)-2-ethylpropyl ether and thioether
3-(4-Fluorophenoxy)benzyl 2-(3,4-dimethylphenyl)-2-methylpropyl ether and thioether
3-Phenoxybenzyl 2-(3,4-methylenedioxyphenyl)-2-methylpropyl ether and thioether
3-Phenoxybenzyl 2-(3,4-methylenedioxyphenyl)-2-ethylpropyl ether and thioether
3-(4-Methoxyphenoxy)benzyl 2-(4-methylthiophenyl)-2-methylpropyl ether and thioether
3-(3-Chlorophenoxy)benzyl 2-(4-chlorophenyl)-2-methylpropyl ether and thioether
3-(3-Chlorophenoxy)benzyl 2-(4-chlorophenyl)-2-ethylpropyl ether and thioether
3-(3-Fluorophenoxy)benzyl 2-(4-chlorophenyl)-2-methylpropyl ether and thioether
3-(3-Fluorophenoxy)benzyl 2-(4-chlorophenyl)-2-ethylpropyl ether and thioether
3-(4-Fluorophenoxy)benzyl 2-(4-difluoromethoxyphenyl)-2-methylpropyl ether and thioether
3-(4-Fluorophenoxy)benzyl 2-(4-difluoromethoxyphenyl)-2-ethylpropyl ether and thioether
5-Benzyl-3-furylmethyl 2-(4-chlorophenyl)-2-methylpropyl ether and thioether
5-Benzyl-3-furylmethyl 2-(4-chlorophenyl)-2-ethylpropyl ether and thioether
3-(4-methoxyphenoxy)benzyl 2-phenyl-2-methylpropyl ether and thioether
3-(4-Methoxyphenoxy)benzyl 2-phenyl-2-ethylpropyl ether and thioether
3-(2-Fluorophenoxy)benzyl 2-(4-chlorophenyl)-2-methylpropyl ether and thioether
3-(4-Fluorophenoxy)benzyl 2-(3-chloro-4-methylphenyl)-2-methylpropyl ether and thioether
3-Phenylthiobenzyl 2-(4-chlorophenyl)-2-methylpropyl ether and thioether
3-Phenoxybenzyl 2-(4-trifluoromethylthiophenyl)-2-methylpropyl ether and thioether
3-(4-Bromophenoxy)benzyl 2-(4-fluorophenyl)-2-ethylpropyl ether and thioether
3-(4-Bromophenoxy)benzyl 2-(4-fluorophenyl)-2-methylpropyl ether and thioether
3-Phenoxybenzyl 2-(4-trifluoromethylphenyl)-2-methylpropyl ether and thioether
3-Phenoxybenzyl 2-(4-trifluoromethylphenyl)-2-ethylpropyl ether and thioether 3-Phenoxybenzyl 2-(4-trifluoromethylthiophenyl)-2-ethylpropyl ether and thioether 3-(4-Fluorophenoxy)benzyl 2-(3,4-dichlorophenyl)-2-methylpropyl ether and thioether 3-(4-Fluorophenoxy)benzyl 2-(3,4-dichlorophenyl)-2-ethylpropyl ether and thioether 3-Phenoxybenzyl 2-(4-difluoromethoxyphenyl)-2-methylpropyl ether and thioether 3-(4-Fluorophenoxy)benzyl 2-(4-difluoromethylthiophenyl)-2-methylpropyl ether and thioether 3-Phenoxybenzyl 2-(4-difluoromethoxyphenyl)-2-ethylpropyl ether and thioether 3-Phenoxybenzyl 2-(3,4-dimethoxyphenyl)-2-methylpropyl ether and thioether 3-(4-Chlorophenoxy)benzyl 2-(4-cyanophenyl)-2-methylpropyl ether and thioether 3-(3-Fluorophenoxy)benzyl 2-(3,4-difluorophenyl)-2-ethylpropyl ether and thioether 3-(4-Methylphenoxy)benzyl 2-(4-chlorophenyl)-2-methylpropyl ether and thioether 3-(4-Methylphenoxy)benzyl 2-(4-chlorophenyl)-2-ethylpropyl ether and thioether 3-Phenoxybenzyl 2-(4-chlorophenyl)-2-methylpropyl ether and thioether 3-(2-Bromophenoxy)benzyl 2-(3,4-dibromophenyl)-2-methylpropyl ether and thioether 3-(2-Chlorophenoxy)benzyl 2-(4-trifluoromethoxyphenyl)-2-methylpropyl ether and thioether 3-(3-Methoxyphenoxy)benzyl 2-(4-ethylphenyl)-2-methylpropyl ether and thioether 3-(2-Methylphenoxy)benzyl 2-(4-isopropylphenyl)-2-methylpropyl ether and thioether 3-(4-Bromophenoxy)benzyl 2-(3,4-dichlorophenyl)-2-methylpropyl ether and thioether 3-(4-Fluorophenoxy)benzyl 2-(4-trifluoromethylthiophenyl)-2-methylpropyl ether and thioether 3-(4-Bromophenoxy)benzyl 2-(3,4-dichlorophenyl)-2-ethylpropyl ether and thioether 3-(3-Bromophenoxy)benzyl 2-(1,2,3,4-tetrahydronaphthalen-7-yl)-2-methylpropyl ether and thioether 3-(4-Chlorobenzyl)benzyl 2-(4-ethoxyphenyl)-2-methylpropyl ether and thioether 3-(3,5-Dichlorophenoxy)benzyl 2-(indan-5-yl)-2-methylpropyl ether and thioether 3-Phenoxybenzyl 2-(4-difluoromethylthiophenyl)-2-methylpropyl ether and thioether 3-Phenoxybenzyl 2-(4-difluoromethylthiophenyl)-2-ethylpropyl ether and thioether 3-Benzoylbenzyl 2-(4-chlorophenyl)-2-methylpropyl ether and thioether 3-Benzoylbenzyl 2-(4-chlorophenyl)-2-ethylpropyl ether and thioether 3-(4-Fluorophenoxy)benzyl 2-(3-trifluoromethylphenyl)-2-methylpropyl ether and thioether 3-(3-Fluorophenylthio)benzyl 2-(3-methylphenyl)-2-methylpropyl ether and thioether 3-Phenoxybenzyl 2-(4-methylthiophenyl)-2-methylpropyl ether and thioether 3-Phenoxybenzyl 2-(4-methylthiophenyl)-2-ethylpropyl ether and thioether 3-Phenoxybenzyl 2-(4-pentafluoroethoxyphenyl)-2-methylpropyl ether and thioether 3-Phenoxybenzyl 2-(3,4-difluoromethylenedioxyphenyl)-2-methylpropyl ether and thioether 3-(4-Fluorophenoxy)benzyl 2-(4-pentafluoroethoxyphenyl)-2-methylpropyl ether and thioether 3-(3-Chlorophenoxy)benzyl 2-(4-difluoromethoxyphenyl)-2-methylpropyl ether and thioether 3-(3-Chlorophenoxy)benzyl 2-(4-difluoromethoxyphenyl)-2-ethylpropyl ether and thioether 3-(4-Chloro-2-methylphenoxy)benzyl 2-(4-allylphenyl)-2-methylpropyl ether and thioether 3-(3,5-Dichlorobenzoyl)benzyl 2-(4-tert-butylphenyl)-2-methylpropyl ether and thioether 3-(4-Chlorophenoxy)benzyl 2-(3-chloro-4-fluorophenyl)-2-methylpropyl ether and thioether 3-(3-Methylphenoxy)benzyl 2-(4-chlorophenyl)-2-methylpropyl ether and thioether 3-(3-Methylphenoxy)benzyl 2-(4-chlorophenyl)-2-ethylpropyl ether and thioether 3-(2-Methoxyphenoxy)benzyl 2-(4-methoxymethylphenyl)-2-methylpropyl ether and thioether 3-(4-Methoxyphenoxy)benzyl 2-(4-methoxyphenyl)-2-methylpropyl ether and thioether 3-(3-Bromophenoxy)benzyl 2-(3-methoxy-4-methylphenyl)-2-methylpropyl ether and thioether 3-(4-Fluorobenzyl)benzyl 2-(4-chlorophenyl)-2-methylpropyl ether and thioether 3-(3,4-Dichlorophenoxy)benzyl 2-(4-isobutyrylphenyl)-2-methylpropyl ether and thioether 3-(4-Fluorophenoxy)benzyl 2-phenyl-2-methylpropyl ether and thioether 3-(4-Fluorophenoxy)benzyl 2-phenyl-2-ethylpropyl ether and thioether 3-(3-Chloro-5-methoxyphenoxy)benzyl 2-[(3,4-di-tert-butyl)phenyl]-2-methylpropyl ether and thioether 3-(3-Chlorophenoxy)benzyl 2-(3-methylphenyl)-2-methylpropyl ether and thioether 3-(4-Fluorophenylthio)benzyl 2-(4-chlorophenyl)-2-methylpropyl ether and thioether 3-(4-Bromophenoxy)benzyl 2-(4-difluoromethoxyphenyl)-2-methylpropyl ether and thioether 3-(4-bromophenoxy)benzyl 2-(4-difluoromethoxyphenyl)-2-ethylpropyl ether and thioether 3-(4-Fluorophenoxy)benzyl 2-(4-tert-butylphenyl)-2-methylpropyl ether and thioether 3-Phenoxybenzyl 2-(2-naphthyl)-2-methylpropyl ether and thioether 3-(4-Fluorophenoxy)benzyl 2-(4-isopropenylphenyl)-2-methylpropyl ether and thioether.

3-Phenoxybenzyl 2-(2-naphthyl)-2-ethylpropyl ether and thioether 3-(4-Fluorophenoxy)benzyl 2-(4-methoxyphenyl)-2-methylpropyl ether and thioether 3-(4-Fluorophenoxy)benzyl 2-(4-methoxyphenyl)-2-ethylpropyl ether and thioether 3-(4-Fluorophenoxy)benzyl 2-(4-chloro-3-methylphenyl)-2-methylpropyl ether and thioether 3-Phenoxybenzyl 2-[3,4-bis(trifluoromethoxy)phenyl]-2-methylpropyl ether and thioether 3-Phenoxybenzyl 2-(4-methoxy-3,5-dimethylphenyl)-2-methylpropyl ether and thioether 3-(4-Bromophenoxy)benzyl 2-(4-methylphenyl)-2-methylpropyl ether and thioether 3-Phenoxybenzyl 2-[4-(2,2-dichlorovinyloxy)phenyl]-2-methylpropyl ether and thioether 3-(4-Methoxyphenoxy)benzyl 2-(4-chlorophenyl)-2-methylpropyl ether and thioether 3-Phenoxybenzyl 2-[4-(1,1,2,2-tetrafluoroethoxy)phenyl]-2-methylpropyl ether and thioether 3-Benzylbenzyl 2-(4-chlorophenyl)-2-methylpropyl ether and thioether 3-Phenoxybenzyl 2-[4-(1,1,2,2-tetrafluoroethoxy)phenyl]-2-ethylpropyl ether and thioether 3-(4-Fluorophenoxy)benzyl 2-(3-methylphenyl)-2-methylpropyl ether and thioether 3-Phenoxybenzyl 2-(4-chlorophenyl)-2-ethylpropyl ether and thioether
3-Phenoxybenzyl 2-(3,4-dichlorophenyl)-2-methylpropyl ether and thioether
3-Phenoxybenzyl 2-(3,4-dichlorophenyl)-2-ethylpropyl ether and thioether
3-Phenoxybenzyl 2-(4-chloro-3-bromophenyl)-2-methylpropyl ether and thioether
3-(3-Chlorophenoxy)benzyl 2-(3,4-dichlorophenyl)-2-methylpropyl ether and thioether
3-(3-Chlorophenoxy)benzyl 2-(3,4-dichlorophenyl)-2-ethylpropyl ether and thioether
3-Phenoxybenzyl 2-(4-chloro-3-bromophenyl)-2-ethylpropyl ether and thioether
3-Phenoxybenzyl 2-[4-(2,2,2-trifluoroethoxy)phenyl]-2-methylpropyl ether and thioether
3-Phenoxybenzyl 2-[4-(2,2,2-trifluoroethoxy)phenyl]-2-ethylpropyl ether and thioether
3-Phenoxybenzyl 2-(3-trifluoromethylphenyl)-2-methylpropyl ether and thioether
3-Phenoxybenzyl 2-(3-chloro-4-methoxyphenyl)-2-methylpropyl ether and thioether
3-(4-Methoxyphenoxy)benzyl 2-(4-bromophenyl)-2-methylpropyl ether and thioether
3-(4-Methoxyphenoxy)benzyl 2-(3,4-dichlorophenyl)-2-methylpropyl ether and thioether
3-Phenoxybenzyl 2-(6-methyl-2-naphthyl)-2-methylpropyl ether and thioether
3-(4-Fluorophenoxy)benzyl 2-(3-bromo-4-chlorophenyl)-2-methylpropyl ether and thioether
3-Phenoxybenzyl 2-[4-(2,2-dichlorovinyl)phenyl]-2-methylpropyl ether and thioether
3-(4-Bromophenoxy)benzyl 2-(3-trifluoromethylphenyl)-2-methylpropyl ether and thioether
3-Phenoxybenzyl 2-(4-nitrophenyl)-2-methylpropyl ether and thioether
3-Phenoxybenzyl 2-(4-nitrophenyl)-2-ethylpropyl ether and thioether
3-(4-Fluorophenoxy)benzyl 2-(3-fluoro-4-methylphenyl)-2-methylpropyl ether and thioether
3-(4-Methoxyphenoxy)benzyl 2-(4-methylphenyl)-2-methylpropyl ether and thioether
3-(4-Fluorophenoxy)benzyl 2-(3,4-diethylphenyl)-2-methylpropyl ether and thioether
3-Phenoxybenzyl 2-(4-dichlorofluoromethoxyphenyl)-2-methylpropyl ether and thioether
3-Phenoxybenzyl 2-(4-dichlorofluoromethoxyphenyl)-2-ethylpropyl ether and thioether
3-Phenoxybenzyl 2-(4-methylphenyl)-2-methylpropyl ether and thioether
3-Phenoxybenzyl 2-(4-bromophenyl)-2-ethylpropyl ether and thioether
3-Phenoxybenzyl 2-(3-chloro-4-methylphenyl)-2-methylpropyl ether and thioether
3-Phenoxybenzyl 2-(3,4-dibromophenyl)-2-methylpropyl ether and thioether
3-Phenoxybenzyl 2-(4-tert-butylphenyl)-2-methylpropyl ether and thioether
3-Phenoxybenzyl 2-(4-fluorophenyl)-2-methylpropyl ether and thioether
3-Phenoxybenzyl 2-(4-bromophenyl)-2-methylpropyl ether and thioether
3-Phenoxybenzyl 2-(4-ethylphenyl)-2-methylpropyl ether and thioether
3-Phenoxybenzyl 2-(4-fluorophenyl)-2-ethylpropyl ether and thioether
3-Phenoxybenzyl 2-(3-chloro-4-fluorophenyl)-2-ethylpropyl ether and thioether
3-Phenoxybenzyl 2-(4-ethylphenyl)-2-ethylpropyl ether and thioether
3-Phenoxybenzyl 2-(4-chloro-3-methylphenyl)-2-methylpropyl ether and thioether
3-Phenoxybenzyl 2-(4-tert-butylphenyl)-2-ethylpropyl ether and thioether
3-Phenoxybenzyl 2-(3,4-dimethylphenyl)-2-methylpropyl ether and thioether
3-Phenoxybenzyl 2-(3-chloro-4-methylphenyl)-2-ethylpropyl ether and thioether
3-Phenoxybenzyl 2-(3,4-dibromophenyl)-2-ethylpropyl ether and thioether
3-Phenoxybenzyl 2-(4-chloro-3-methylphenyl)-2-ethylpropyl ether and thioether
3-Phenoxybenzyl 2-(3,4-dimethylphenyl)-2-ethylpropyl ether and thioether
3-Phenoxybenzyl 2-(4-methylphenyl)-2-ethylpropyl ether and thioether
3-Phenoxybenzyl 2-(3-chloro-4-fluorophenyl)-2-methylpropyl ether and thioether
3-Phenoxybenzyl 2-(3,4-difluorophenyl)-2-methylpropyl ether and thioether
3-Phenoxybenzyl 2-(3,4-difluorophenyl)-2-ethylpropyl ether and thioether
3-Phenoxybenzyl 2-(3-bromo-4-fluorophenyl)-2-methylpropyl ether and thioether
3-Phenoxybenzyl 2-(3-bromo-4-fluorophenyl)-2-ethylpropyl ether and thioether
3-Phenoxybenzyl 2-(3-fluoro-4-bromophenyl)-2-methylpropyl ether and thioether
3-Phenoxybenzyl 2-(3-fluoro-4-bromophenyl)-2-ethylpropyl ether and thioether
3-Phenoxybenzyl 2-(4-bromo-3-chlorophenyl)-2-methylpropyl ether and thioether
3-Phenoxybenzyl 2-(4-bromo-3-chlorophenyl)-2-ethylpropyl ether and thioether
3-Phenoxybenzyl 2-(4-fluoro-3-methylphenyl)-2-methylpropyl ether and thioether
3-Phenoxybenzyl 2-(4-fluoro-3-methylphenyl)-2-ethylpropyl ether and thioether
3-Phenoxybenzyl 2-(3-fluoro-4-methylphenyl)-2-methylpropyl ether and thioether
3-Phenoxybenzyl 2-(3-fluoro-4-methylphenyl)-2-ethylpropyl ether and thioether
3-Phenoxybenzyl 2-(3-bromo-4-methylphenyl)-2-methylpropyl ether and thioether
3-Phenoxybenzyl 2-(3-bromo-4-methylphenyl)-2-ethylpropyl ether and thioether
3-Phenoxybenzyl 2-(3,4-diethylphenyl)-2-methylpropyl ether and thioether
3-Phenoxybenzyl 2-(3,4-diethylphenyl)-2-ethylpropyl ether and thioether
3-Phenoxybenzyl 2-(4-isopropylphenyl)-2-methylpropyl ether and thioether
3-Phenoxybenzyl 2-(4-isopropylphenyl)-2-ethylpropyl ether and thioether
3-Phenoxybenzyl 2-(3,4-diisopropylphenyl)-2-methylpropyl ether and thioether
3-Phenoxybenzyl 2-(3,4-diisopropylphenyl)-2-ethylpropyl ether and thioether
3-Phenoxybenzyl 2-(3,4-di-tert-butylphenyl)-2-methylpropyl ether and thioether
3-Phenoxybenzyl 2-(3,4-di-tert-butylphenyl)-2-ethylpropyl ether and thioether
3-Phenoxybenzyl 2-(3-ethyl-4-methylphenyl)-2-methylpropyl ether and thioether
3-Phenoxybenzyl 2-(3-ethyl-4-methylphenyl)-2-ethylpropyl ether and thioether 3-Phenoxybenzyl 2-(4-ethyl-3-methylphenyl)-2-methylpropyl ether and thioether
3-Phenoxybenzyl 2-(4-ethyl-3-methylphenyl)-2-ethylpropyl ether and thioether
3-Phenoxybenzyl 2-(4-tert-butyl-3-methylphenyl)-2-methylpropyl ether and thioether
3-Phenoxybenzyl 2-(4-tert-butyl-3-methylphenyl)-2-ethylpropyl ether and thioether
3-Phenoxybenzyl 2-(4-isopropyl-3-methylphenyl)-2-methylpropyl ether and thioether
3-Phenoxybenzyl 2-(4-isopropyl-3-methylphenyl)-2-ethylpropyl ether and thioether
3-Phenoxybenzyl 2-(4-cyanophenyl)-2-methylpropyl ether and thioether
3-Phenoxybenzyl 2-(4-cyanophenyl)-2-ethylpropyl ether and thioether
3-Phenoxybenzyl 2-(4-ethoxyphenyl)-2-methylpropyl ether and thioether
3-Phenoxybenzyl 2-(4-ethoxyphenyl)-2-ethylpropyl ether and thioether
3-Phenoxybenzyl 2-(3,5-dichlorophenyl)-2-methylpropyl ether and thioether
3-Phenoxybenzyl 2-(3,5-dichlorophenyl)-2-ethylpropyl ether and thioether
3-Phenoxybenzyl 2-[4-(n-propoxy)phenyl]-2-methylpropyl ether and thioether
3-Phenoxybenzyl 2-[4-(n-propoxy)phenyl]-2-ethylpropyl ether and thioether
3-(4-Fluorophenoxy)benzyl 2-(3-chloro-4-fluorophenyl)-2-methylpropyl ether and thioether
3-(4-Fluorophenoxy)benzyl 2-(3-chloro-4-fluorophenyl)-2-ethylpropyl ether and thioether
3-Phenoxybenzyl 2-(4-isopropoxyphenyl)-2-methylpropyl ether and thioether
3-Phenoxybenzyl 2-(4-isopropoxyphenyl)-2-ethylpropyl ether and thioether
3-Phenoxybenzyl 2-(4-acetylphenyl)-2-methylpropyl ether and thioether
3-Phenoxybenzyl 2-(4-acetylphenyl)-2-ethylpropyl ether and thioether
3-Phenoxybenzyl 2-(4-cyclopentyloxyphenyl)-2-methylpropyl ether and thioether
3-Phenoxybenzyl 2-(4-cyclopentyloxyphenyl)-2-ethylpropyl ether and thioether
3-Phenoxybenzyl 2-[4-(n-pentyloxy)phenyl]-2-methylpropyl ether and thioether
3-Phenoxybenzyl 2-[4-(n-pentyloxy)phenyl]-2-ethylpropyl ether and thioether
3-Phenoxybenzyl 2-(4-isobutyloxyphenyl)-2-methylpropyl ether and thioether
3-Phenoxybenzyl 2-(4-isobutyloxyphenyl)-2-ethylpropyl ether and thioether
3-Phenoxybenzyl 2-(4-iodophenyl)-2-methylpropyl ether and thioether
3-Phenoxybenzyl 2-(4-iodophenyl)-2-ethylpropyl ether and thioether
3-(4-Bromophenoxy)benzyl 2-(4-ethoxyphenyl)-2-methylpropyl ether and thioether
3-(4-Bromophenoxy)benzyl 2-(4-ethoxyphenyl)-2-ethylpropyl ether and thioether
3-Phenoxybenzyl 2-(4-vinyloxyphenyl)-2-methylpropyl ether and thioether
3-Phenoxybenzyl 2-(4-vinyloxyphenyl)-2-ethylpropyl ether and thioether
3-Phenoxybenzyl 2-(4-biphenyl)-2-methylpropyl ether and thioether
3-Phenoxybenzyl 2-(4-biphenyl)-2-ethylpropyl ether and thioether
3-Phenoxybenzyl 2-[4-(n-butoxy)phenyl]-2-methylpropyl ether and thioether
3-Phenoxybenzyl 2-[4-(n-butoxy)phenyl]-2-ethylpropyl ether and thioether
3-Phenoxybenzyl 2-[4-(sec-butoxy)phenyl]-2-methylpropyl ether and thioether
3-Phenoxybenzyl 2-[4-(sec-butoxy)phenyl]-2-ethylpropyl ether and thioether
3-Phenoxybenzyl 2-(4-phenoxyphenyl)-2-methylpropyl ether and thioether
3-Phenoxybenzyl 2-(4-phenoxyphenyl)-2-ethylpropyl ether and thioether
3-Phenoxybenzyl 2-(4-cyclohexyloxyphenyl)-2-methylpropyl ether and thioether
3-Phenoxybenzyl 2-(4-cyclohexyloxyphenyl)-2-ethylpropyl ether and thioether
3-Phenoxybenzyl 2-[4-(1,1-difluoro-2-iodoethoxy)phenyl]-2-methylpropyl ether and thioether
3-Phenoxybenzyl 2-[4-(1,1-difluoro-2-iodoethoxy)phenyl]-2-ethylpropyl ether and thioether
3-(4-Fluorophenoxy)benzyl 2-(4-isopropylphenyl)-2-methylpropyl ether and thioether
3-(4-Fluorophenoxy)benzyl 2-(4-isopropylphenyl)-2-ethylpropyl ether and thioether
3-Phenoxybenzyl 2-(3-chloro-4-ethoxyphenyl)-2-methylpropyl ether and thioether
3-Phenoxybenzyl 2-(3-chloro-4-ethoxyphenyl)-2-ethylpropyl ether and thioether
3-Phenoxybenzyl 2-[4-(1,1-difluoroethoxy)phenyl]-2-methylpropyl ether and thioether
3-Phenoxybenzyl 2-[4-(1,1-difluoroethoxy)phenyl]-2-ethylpropyl ether and thioether
3-Phenoxybenzyl 2-(4-methoxymethylphenyl)-2-methylpropyl ether and thioether
3-Phenoxyphenyl 2-(4-methoxymethylphenyl)-2-ethylpropyl ether and thioether
3-Phenoxybenzyl 2-(4-ethoxymethoxyphenyl)-2-methylpropyl ether and thioether
3-Phenoxybenzyl 2-(4-ethoxymethoxyphenyl)-2-ethylpropyl ether and thioether
3-Phenoxybenzyl 2-(4-ethoxymethylphenyl)-2-methylpropyl ether and thioether
3-Phenoxybenzyl 2-(4-ethoxymethylphenyl)-2-ethylpropyl ether and thioether
3-Phenoxybenzyl 2-(4-methoxymethoxyphenyl)-2-methylpropyl ether and thioether
3-Phenoxybenzyl 2-(4-methoxymethoxyphenyl)-2-ethylpropyl ether and thioether
3-Phenoxybenzyl 2-[4-(1-ethoxyethyl)phenyl]-2-methylpropyl ether and thioether
3-Phenoxybenzyl 2-[4-(1-ethoxyethyl)phenyl]-2-ethylpropyl ether and thioether
3-Phenoxybenzyl 2-(4-ethoxycarbonylphenyl)-2-methylpropyl ether and thioether
3-Phenoxybenzyl 2-(4-ethoxycarbonylphenyl)-2-ethylpropyl ether and thioether
3-Phenoxybenzyl 2[4-(1-methoxyethyl)phenyl]-2-methylpropyl ether and thioether
3-Phenoxybenzyl 2-[4-(1-methoxyethyl)phenyl]-2-ethylpropyl ether and thioether
3-Phenoxybenzyl 2-(4-isopropenylphenyl)-2-methylpropyl ether and thioether
3-Phenoxybenzyl 2-(4-isopropenylphenyl)-2-ethylpropyl ether and thioether
3-Phenoxybenzyl 2-[4-(2-ethoxyethoxy)phenyl]-2-methylpropyl ether and thioether
3-Phenoxybenzyl 2-4-(2-ethoxyethoxy)phenyl-2-ethylpropyl ether and thioether 3-Phenoxybenzyl 2-(4-ethoxy-3-methylphenyl)-2-methylpropyl ether and thioether
3-Phenoxybenzyl 2-(4-ethoxy-3-methylphenyl)-2-ethylpropyl ether and thioether
3-Phenoxybenzyl 2-[4-(2-methyl-1-propenyl)phenyl]-2-methylpropyl ether and thioether
3-Phenoxybenzyl 2-[4-(2-methyl-propenyl)phenyl]-2-ethylpropyl ether and thioether
3-Phenoxybenzyl 2-[(1,2,2-trichlorovinyloxy)phenyl]-2-methylpropyl ether and thioether
3-Phenoxybenzyl 2-[(1,2,2-trichlorovinyloxy)phenyl]-2-ethylpropyl ether and thioether
3-Phenoxybenzyl 2-(3,4-diethoxyphenyl)-2-methylpropyl ether and thioether
3-Phenoxybenzyl 2-(3,4-diethoxyphenyl)-2-ethylpropyl ether and thioether
3-(4-Ethoxyphenoxy)benzyl 2-(4-chlorophenyl)-2-methylpropyl ether and thioether
3-(4-Ethoxyphenoxy)benzyl 2-(4-chlorophenyl)-2-ethylpropyl ether and thioether
3-Phenoxybenzyl 2-(4-ethynylphenyl)-2-methylpropyl ether and thioether
3-Phenoxybenzyl 2-(4-ethynylphenyl)-2-ethylpropyl ether and thioether
3-Phenoxybenzyl 2-(4-ethoxy-3,5-dimethylphenyl)-2-methylpropyl ether and thioether
3-Phenoxybenzyl 2-(4-ethoxy-3,5-dimethylphenyl)-2-ethylpropyl ether and thioether
3-Phenoxybenzyl 2-(4-propargyloxyphenyl)-2-methylpropyl ether and thioether
3-Phenoxybenzyl 2-(4-propargyloxyphenyl)-2-ethylpropyl ether and thioether
3-Phenoxybenzyl-2-(4-ethoxy-3-methoxyphenyl)-2-methylpropyl ether and thioether
3-Phenoxybenzyl 2-(4-ethoxy-3-methoxyphenyl)-2-ethylpropyl ether and thioether
3-Phenoxybenzyl 2-(4-ethylthiophenyl)-2-methylpropyl ether and thioether
3-Phenoxybenzyl 2-(4-ethylthiophenyl)-2-ethylpropyl ether and thioether
3-(4-Ethoxyphenoxy)benzyl 2-(4-ethoxyphenyl)-2-methylpropyl ether and thioether
3-(4-Ethoxyphenoxy)benzyl 2-(4-ethoxyphenyl)-2-ethylpropyl ether and thioether
3-Phenoxybenzyl 2-[4-(1-chlorovinyl)phenyl]-2-methylpropyl ether and thioether
3-Phenoxybenzyl 2-[4-(1-chlorovinyl)phenyl]-2-ethylpropyl ether and thioether
3-Phenoxybenzyl 2-(4-vinylphenyl)-2-methylpropyl ether and thioether
3-Phenoxybenzyl 2-[4-(2,2,2-trifluoroethoxycarbonyl)phenyl]-2-methylpropyl ether and thioether
3-Phenoxybenzyl 2-[4-(2,2,2-trifluoroethoxycarbonyl)phenyl]-2-ethylpropyl ether and thioether
3-Phenoxybenzyl 2-[4-(2-chloroethoxy)phenyl]-2-methylpropyl ether and thioether
3-Phenoxybenzyl 2-[4-(2-chloroethoxy)phenyl]-2-ethylpropyl ether and thioether
3-Phenoxybenzyl 2-[4-(1-buten-2-yl)phenyl]-2-methylpropyl ether and thioether
3-Phenoxybenzyl 2-[4-(1-buten-2-yl)phenyl]-2-ethylpropyl ether and thioether
3-Phenoxybenzyl 2-[4-(2-buten-2-yl)phenyl]-2-methylpropyl ether and thioether
3-Phenoxybenzyl 2-[4-(2-buten-2-yl)phenyl]-2-ethylpropyl ether and thioether The preparation processes of the present invention will now be described in detail.

In the case where an alcohol or thiol of the general formula [V] in which A stands for Y-H (in which Y is as defined above) is reacted with a halide of the general formula [VI] in which D stands for a halogen atom, the reaction is carried out in the presence of a base as an acid acceptor in an appropriate solvent at room temperature or under heating to give a desired 2-arylpropyl ether or thioether derivative. As the base, there can be mentioned an alkali metal hydroxide, an alkaline earth metal hydroxide, an alkali metal hydride, an alkali metal alcoholate, an alkali metal oxide, an alkali metal carbonate, sodium amide and triethylamine. Furthermore, silver oxide may be used as the acid acceptor. As the solvent, there can be used, for example, water, aromatic hydrocarbons such as benzene, toluene and xylene, aliphatic hydrocarbons such as hexane, heptane and petroleum benzin, halogenated hydrocarbons such as chloroform and dichloromethane, aprotic polar solvents such as dimethylformamide and dimethylsulfoxide, ethers such as diisopropyl ether, diethyl ether, 1,2-dimethoxyethane, tetrahydrofuran and dioxane, nitriles such as acetonitrile and propionitrile, and ketones such as diisopropyl ketone. If a phase transfer catalyst represented by tetra-n-butyl ammonium bromide or triethylbenzyl ammonium chloride is used as the catalyst, the intended 2-arylpropyl ether or thioether derivative can be obtained in a high yield.

In the case where an alcoholate or thioalcoholate of the general formula [V] in which A stands for a group Y-M (in which Y is as defined above and M is other than hydrogen) is reacted with a halide of the general formula [VI] in which D stands for a halogen atom, the reaction is carried out in a solvent as mentioned above at room temperature or under heating to give a desired 2-arylpropyl ether or thioether derivative. When the reactivity is low, a catalytic amount of potassium iodide or copper iodide is preferably added.

In the case where a halide of the general formula [V] in which A stands for a halogen atom is reacted with an alcohol or thiol or alcoholate or thioalcoholate of the general formula [VI] in which D stands for a group Y-M (in which Y and M are as defined above), the reaction can be carried out according to the same procedures as described above. Especially when a halide of the general formula [V] in which A stands for a halogen atom is reacted with an alcohol or thiol of the general formula [VI] in which D stands for Y-H (in which Y is as defined above), the reaction is carried out in the presence of a base as an acid acceptor in an aprotic polar solvent, preferably dimethylsulfoxide or sulfolane, under heating, whereby a desired 2-arylpropyl ether or thioether derivative can be obtained in a high yield.

In the case where an alcohol of the general formula [V] in which A stands for a hydroxyl group is reacted with an alcohol of the general formula [VI] in which D stands for a hydroxyl group, dehydration reaction is carried out in the presence of a catalyst to give a 2-arylpropyl ether derivative. As the catalyst, there may be employed an acid catalyst such as sulfuric acid, hydrochloric acid, an aromatic sulfonic acid, sulfonyl chloride, boron trifluoride or aluminum chloride. Furthermore, there may be used iodine, a solid acid catalyst (aluminatitanium oxide or the like), dimethylsulfoxide, alumina, a sulfide or an ion exchange resin as the dehydrating catalyst. The reaction is preferably carried out under reflux in an inert solvent azeotropic with water, such as benzene or toluene, according to need.

Furthermore, a 2-arylpropyl ether derivative can be obtained by reacting an alcohol of the general formula [V] in which A stands for a hydroxyl group with an alcohol of the general formula [VI] in which D stands for a hydroxyl group in the presence of a dehydrating agent, if necessary in the presence of a catalyst. As the dehydrating agent, there is preferably used an N,N-substituted carbodiimide, especially N,N-dicyclohexylcarbodiimide. For example, cuprous chloride is preferably used as the catalyst. The reaction is carried out in an appropriate inert solvent or diluent at room temperature or under heating. As the solvent or diluent, there may preferably be used ethers such as 1,2-diethoxyethane, dioxane and tetrahydrofuran, aprotic polar solvents such as dimethylformamide, hexamethylphosphoric triamide and dimethylsulfoxide, and ketones such as acetone, methylethyl ketone and cyclohexanone.

As another process for the preparation of 2-arylpropyl ether derivatives, there can be mentioned a process in which a metal alcoholate or sulfonic acid ester of an alcohol of the general formula [V] in which A stands for a hydroxyl group is reacted with an alcohol of the general formula [VI] in which D stands for a hydroxyl group, and a process in which an alcohol of the general formula [V] in which A stands for a hydroxyl group is reacted with a metal alcoholate or sulfonic acid ester of an alcohol of the general formula [VI]. However, these processes are disadvantageous from the viewpoint of the yield of the desired product compound.

The starting substance represented by the general formula [V] can be prepared according to a known process or a process similar to a known process disclosed in a reference. For example, an alcohol represented by the general formula [V] in which A stands for a hydroxyl group can be obtained by alkylating a corresponding arylacetonitrile of the formula Ar.CH$_2$.CN, in which Ar is as defined above, with a halogenated alkyl compound, hydrolyzing the obtained nitrile to a corresponding carboxylic acid and reducing the carboxylic acid. Furthermore, a halogenated compound of the general formula [V] in which A stands for a halogen atom, obtained by adding a 2-alkylallyl halide to an aryl compound, can be converted to an alcohol as mentioned above.

The preparation routes are diagrammatically shown below.

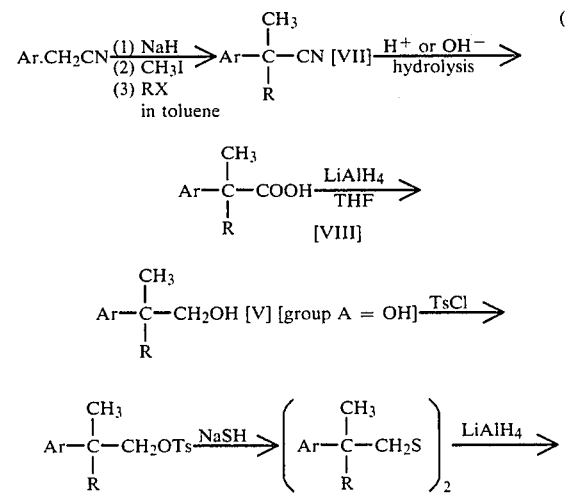

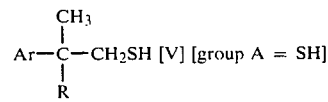

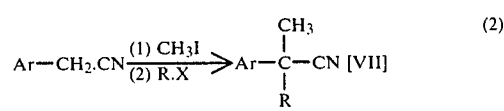

50% NaOH or KOH, phase transfer catalyst
Reference: Roczniki Chem., 39 (9), 1223 (1965) (Pol) [Chemical Abstract 64, 12595h (1966)]
Then, the preparation route (1) is adopted.

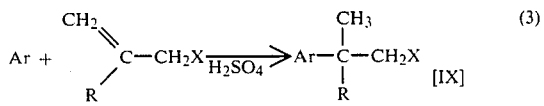

(A in formula [V] is a halogen atom)
Reference: Chem. Ber., 94, 2609 (1961)

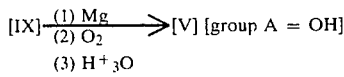

Reference: J. Am. Chem. Soc., 65, 1469 (1943)

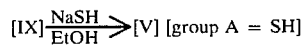

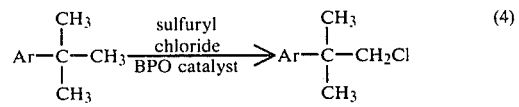

Reference: Chem. Ber., 94, 2609 (1961) [V] in which group A is OH or SH is synthesized according to route (3).

Furthermore, an alcohol of the general formula [V] in which A stands for a hydroxyl group may be prepared according to the process disclosed in Helvetica Chimica Acta, 54, 868 (1971).

A metal alcoholate or metal thioalcoholate of the general formula [V] in which A stands for a group Y-M in which Y is as defined above and M is other than hydrogen can easily be prepared according to a conventional method, for example, a process comprising reacting an alcohol or thiol of the general formula [V] in which A stands for a group Y-M in which Y is as defined above and M is a hydrogen atom with a metal hydride such as sodium hydride.

An alcohol of the general formula [VI] in which D stands for a hydroxyl group is known as an alcohol component of a synthetic pyrethroid or it may be prepared according to a known process disclosed in a reference. A thiol of the general formula [VI] in which D stands for Y-H in which Y stands for a sulfur atom is prepared from a corresponding alcohol according to a conventional method.

The process for the preparation of 2-arylpropyl ether and thioether derivatives of the present invention will now be described in detail with reference to the following Synthesis Examples.

SYNTHESIS EXAMPLE 1

(Etherification Process A)

Preparation of 3-(4-methoxyphenoxy)benzyl 2-(4-methylphenyl)-2-methylpropyl ether is described To 20 ml of dry acetonitrile was added 0.90 g of sodium hydride (60% in oil), and a solution of 2.5 g of 2-(4-methylphenyl)-2-methylpropyl alcohol in 10 ml of acetonitrile was added dropwise to the mixture at 50° C. The mixture was refluxed for 30 minutes, and a solution of 5.3 g of 3-(4-methoxyphenoxy)benzyl bromide in 10 ml of acetonitrile was added dropwise to the reaction mixture over a period of 10 minutes. The mixture was further refluxed for 1 hour, and the mixture was cooled to room temperature, poured into water and was extracted with toluene. The toluene extract was washed with a saturated aqueous solution of sodium chloride and dried over $Na_2SO_4$, and evaporated under reduced pressure, and the obtained crude ether was purified by column chromatography on 150 g of silica gel (1:1 mixed solvent of toluene and n-hexane was used as eluent) to give 3.4 g of the desired ether (the yield was 59% of the theoretical yield).

$n_D^{20}$ 1.5750.

$\nu_{max}^{film}$ (cm$^{-1}$) 1590, 1510, 1490, 1245, 1215, 1105, 1040, 815

$\delta CCl_4$ (ppm): 1.30 (s, 6H), 2.28 (s, 3H), 3.35 (s, 2H), 3.75 (s, 3H), 4.38 (s, 2H), 6.7–7.3 (m, 12H)

Elementary Analysis Values as $C_{25}H_{28}O_3$: Calculated: C=79.75%, H=7/50% Found: C=79.99%, H=7.48%

SYNTHESIS EXAMPLE 2

(Etherification Process B)

Preparation of 3-(4-fluorophenoxy)benzyl 2-(3,4-dichlorophenyl)-2-methylpropyl ether is described To 20 ml of toluene was added 0.63 g of sodium hydride (60% in oil) and the mixture was refluxed, and a solution of 2.3 g of 2-(3,4-dichlorophenyl)-2-methylpropyl alcohol in 10 ml of 25% DMF/toluene was added dropwise to the mixture over a period of 15 minutes. The mixture was stirred for 15 minutes, and a solution of 3.5 g of 3-(4-fluorophenoxy)benzyl bromide in 10 ml of toluene was added dropwise to the mixture over a period of 20 minutes. Then, the mixture was refluxed for 1 hour and cooled to room temperature, and poured into water.

The organic layer was separated, washed with water and dried over $Na_2SO_4$, and evaporated under reduced pressure, and the obtained crude ether was purified by column chromatography on 100 g of silica gel (1:1 mixed solvent of toluene and n-hexane was used as eluent) to give 3.1 g of the desired ether (the yield was 74% of the theoretical yield).

$n_D^{20}$ 1.5732

$\nu_{max}^{film}$ (cm$^{-1}$): 1590, 1505, 1490, 1265, 1205, 1100, 1035, 695, $\delta CCl_4$ (ppm): 1.30 (s, 6H), 3.34 (s, 2H), 4.38 (s, 2H), 6.7–7.4 (m, 11H).

Elementary Analysis Values as $C_{23}H_{21}Cl_2FO_2$: Calculated: C=69.09%, H=5.29%, Cl=8.87%, F=4.75%, Found: C=68.88%, H=5.34%, Cl=8.75%, F=4.57%.

SYNTHESIS EXAMPLE 3

(Etherification Process C)

Preparation of 3-(4-methylphenoxy)benzyl 2-(4-chlorophenyl)-2-methylpropyl ether is described To 15.0 g of a 50% aqueous solution of NaOH were added 6.0 g of 2-(4-chlorophenyl)-2-methylpropyl alcohol, 8.1 g of 3-(4-methylphenoxy)benzyl chloride and 1.1 g of tetrabutyl ammonium bromide, and the mixture was stirred at 80° C. for 1 hour. The mixture was cooled to room temperature and water was added, and the mixture was extracted with toluene and the toluene extract was washed with water and dried over $Na_2SO_4$, and evaporated under reduced pressure, and the obtained crude ether was purified by column chromatography on 250 g of silica gel (1:1 mixed solvent of toluene and n-hexane was used as eluent) to give 9.9 g of the desired ether (the yield was 80% of the theoretical yield).

$n_D^{20}$ 1.5741

$\nu_{max}^{film}$ (cm$^{-1}$): 1595, 1510, 1455, 1260, 1215, 1110, 1015, 830, 695, $\delta CCl_4$ (ppm): 1.29 (s, 6H), 2.31 (s, 3H), 3.32 (s, 2H), 4.35 (s, 2H), 6.7–7.3 (m, 12H).

Elementary Analysis Values as $C_{24}H_{25}ClO_2$: Calculated: C=75.68%, H=6.61%, Cl=9.31% Found: C=75.86%, H=6.42%, Cl=9.22%

SYNTHESIS EXAMPLE 4

(Etherification Process D)

Preparation of 3-(4-fluorophenoxy)benzyl 2-(4-fluorophenyl)-2-methylbutyl ether is described To 20 ml of toluene were added 2 ml of concentrated sulfuric acid, 2.7 g of 3-(4-fluorophenoxy)benzyl alcohol and 2.3 g of 2-(4-fluorophenyl)-2-methylbutyl alcohol, and the mixture was refluxed for 6 hours (water formed by reaction was removed). The mixture was cooled to room temperature, and water was added to the mixture and the toluene layer was separated, washed with water, dried, and evaporated under reduced pressure, and the obtained crude ether was purified by column chromatography on 100 g of silica gel (1:1 mixed solvent of toluene and n-hexane was used as eluent) to give 2.2 g of the desired ether (the yield was 46% of the theoretical yield).

$n_D^{20}$ 1.5478

$\nu_{max}^{film}$ (cm$^{-1}$): 1585, 1505, 1230, 1195, 1165, 1100, 830, 780, 690.

$\delta CCl_4$ (ppm): 0.65 (t, J=7.5 Hz, 3H), 1.28 (s, 3H), 1.5–1.9 (m, 2H), 3.37 (s, 2H), 4.35 (s, 2H), 6.7–7.3 (m, 12H).

Elementary Analysis Values as $C_{24}H_{24}F_2O_2$: Calculated: C=75.37%, H=6.32%, F=9.94% Found: C=75.54%, H=6.21%, F=10.01%

SYNTHESIS EXAMPLE 5

(Etherification Process E)

Preparation of 3-phenoxybenzyl 2-(4-difluoromethoxyphenyl)-2-methylpropyl ether is described 2.0 g of 2-(4-difluoromethoxyphenyl)-2-methylpropyl alcohol, 2.0 g of m-phenoxybenzyl chloride, 20 g of 50% NaOH and 0.3 g of triethylbenzyl ammonium bromide were stirred at 50° C. for 2 hours. Then, $H_2O$ and benzene were added to the reaction mixture, and the mixture was sufficiently shaken and the benzene layer was separated, washed with water, dried over Na$_2$SO$_4$, and evaporated under reduced pressure, and the obtained crude ether was purified by column chromatography on 130 g of silica gel (2:3 mixed solvent of toluene and hexane was used as eluent) to give 3.0 g of the desired ether (the yield was 81% of the theoretical yield).

n$_D^{20.5}$ 1.5490

$\nu_{max}^{film}$ (cm$^{-1}$): 1580, 1485, 1380, 1250, 1215, 1130, 1040, 690, $\delta$CCl$_4$ (ppm): 1.32 (s, 6H), 3.36 (s, 2H), 4.21 (s, 2H), 6.38 (t, 1H, J=7 5 Hz), 6.8–7.4 (m, 13H).

SYNTHESIS EXAMPLE 6

Preparation of 3-(4-bromophenoxy)benzyl 2-(4-fluorophenyl)-2-ethylpropyl ether is described To 20 ml of toluene was added 0.60 g of sodium hydride (60% in oil) and the mixture was refluxed, and a solution of 2.0 g of 2-(4-fluorophenyl)-2-methylbutyl alcohol in 10 ml of 40% DMF/toluene was added dropwise to the mixture over a period of 20 minutes. The mixture was stirred for 10 minutes and a solution of 4.0 g of 3-(4-bromophenoxy)benzyl bromide in 10 ml of toluene was added dropwise to the mixture over a period of 10 minutes. The mixture was further heated and refluxed for 1 hour and cooled to room temperature, and poured into water. The toluene layer was separated, washed with water, dried over Na$_2$SO$_4$, and evaporated under reduced pressure and the obtained crude ether was purified by column chromatography on 100 g of silica gel (1:1 mixed solvent of toluene and hexane was used as eluent) to give 3.7 g of the desired ether (the yield was 76% of the theoretical yield).

n$_D^{20.2}$ 1.5778

$\nu_{max}^{film}$ (cm$^{-1}$): 1605, 1580, 1510, 1485, 1250, 1165, 1100, 1070, 1010, 830, $\delta$CCl$_4$ (ppm): 0.67 (t, 3H, J=7.2 Hz), 1.30 (s, 3H), 1.5–1.9 (m, 2H), 3.39 (s, 2H), 4.39 (s, 2H), 6.7–7.5 (m, 12H).

SYNTHESIS EXAMPLE 7

3-Phenoxybenzyl 2-(3,4-methylenedioxyphenyl)-2-methylpropyl ether was synthesized according to the procedures described in Synthesis Example 2 by using 0.4 g of 2-(3,4-methylenedioxyphenyl)-2-methylpropyl alcohol.

n$_D^{20.7}$ 1.5839

$\nu_{max}^{film}$ (cm$^{-1}$): 1590, 1490, 1255, 1105, 1045, 940, $\delta$CCl$_4$ (ppm): 1.28 (s, 6H), 3.32 (s, 2H), 4.41 (s, 2H), 5.82 (s, 2H), 6.5–7.4 (m, 12H).

SYNTHESIS EXAMPLE 8

(Etherification Process F)

Preparation of 3-(4-methoxyphenoxy)benzyl 2-(3,4-dichlorophenyl)-2-methylpropyl ether is described A mixture of 9.98 g of 2-(3,4-dichlorophenyl)-2-methylpropyl chloride, 9.67 g of 4-methoxyphenoxybenzyl alcohol, 3.9 g of 45% sodium hydroxide and 48 g of dimethylsulfoxide was heated and stirred at 140° C. for 3 hours, and 1.8 g of 45% sodium hydroxide was further added, and the reaction was kept at the same temperature for 4 hours, poured into water, and was extracted with benzene. The benzene extract was washed with water, dried over Na$_2$SO$_4$, and evaporated under reduced pressure and the obtained crude ether was purified by column chromatography on 250 g of silica gel (1:1 mixed solvent of toluene and n-hexane was used as eluent) to give 3.34 g of the desired ether (the yield was 78% of the theoretical yield based on consumed 2-(3,4-dichlorophenyl)-2-methylpropyl chloride).

n$_D^{20}$ 1.5830

$\nu_{max}^{film}$ (cm$^{-1}$): 1590, 1510, 1490, 1250, 1220, 1110, 1040, 840, $\delta$CCl$_4$ (ppm): 1.30 (s, 6H), 3.34 (s, 2H), 3.76 (s, 3H), 4.38 (s, 2H), 6.7–7.5 (m, 11H).

SYNTHESIS EXAMPLE 9

3-Phenoxybenzyl 2-(4-methylthiophenyl)-2-methylpropyl ether was synthesized according to the procedures described in Synthesis Example 2.

n$_D^{19.8}$ 1.5921

$\nu_{max}^{film}$ (cm$^{-1}$): 2920, 1580, 1490, 1250, 1215, 1100, 815, 690.

$\delta$CCl$_4$ (ppm): 1.31 (s, 6H), 2.37 (s, 3H), 3.36 (s, 2H), 4.38 (s, 2H), 6.6–7.4 (m, 13H).

SYNTHESIS EXAMPLE 10

3-Phenoxybenzyl 2-(4-chlorophenyl)-2-methylpropyl thioether was synthesized according to the procedures described in Synthesis Example 2.

n$_D^{19.7}$ 1.6074

$\nu_{max}^{film}$ (cm$^{-1}$): 1595, 1505, 1495, 1460, 1265, 1225, 1175, 1110, 1025, 965, 835, $\delta$CCl$_4$(ppm): 1.30 (s, 6H), 2.53 (s, 2H), 3.29 (s, 2H), 6.8–7.3 (m, 13H).

SYNTHESIS EXAMPLE 11

3-Phenoxybenzyl 2-(4-methylphenyl)-2-methylpropyl ether was synthesized according to the procedures described in Synthesis Example 1.

n$_D^{18.5}$ 1.5794

$\nu_{max}^{film}$ (cm$^{-1}$): 1590, 1495, 1260, 1220, 1110, 820, 700, $\delta$CCl$_4$ (ppm): 1.28 (s, 6H), 2.26 (s, 3H), 3.32 (s, 2H), 4.25 (s, 2H), 6.7–7.4 (m, 13H).

Elementary Analysis Values as C$_{24}$H$_{26}$O$_2$: Calculated: C=83.20%, H=7.56% Found: C=83.25%, H=7.59%

SYNTHESIS EXAMPLE 12

3-Phenoxybenzyl 2-(3,4-dichlorophenyl)-2-methylpropyl ether was synthesized according to the procedures described in Synthesis Example 2.

n$_D^{18}$ 1.5890, $\nu_{max}^{film}$ (cm$^{-1}$): 1590, 1490, 1260, 1220, 1110, 1035, 695, $\delta$CCl$_4$ (ppm): 1.32 (s, 6H), 3.34 (s, 2H), 4.40 (s, 2H), 6.8–7.5 (m, 12H).

Elementary Analysis Values as C$_{23}$H$_{22}$Cl$_2$O$_2$: Calculated: C=68.83%, H=5.53%, Cl=16.67%, Found: C=68.78%, H=5.48%, Cl=16.72%.

SYNTHESIS EXAMPLE 13

3-Phenoxybenzyl 2-(4-chlorophenyl)-2-methylpropyl ether was synthesized according to the procedures described in Synthesis Example 3.

n$_D^{17}$ 1.5832

$\nu_{max}^{film}$ (cm$^{-1}$): 1600, 1505, 1270, 1230, 1120, 1025, 840, 705, $\delta$CCl$_4$ (ppm): 1.26 (s, 6H), 3.25 (s, 2H), 4.27 (s, 2H), 6.6–7.3 (m, 13H), Elementary Analysis Values as $C_{23}H_{23}ClO_2$: Calculated: C=75.30%, H=6.32%, Cl=9.66% Found: C=75.18%, H=6.51%, Cl=9.70%

SYNTHESIS EXAMPLE 14

3-Phenoxybenzyl 2-(4-chlorophenyl)-2-ethylpropyl ether was synthesized according to the procedures described in Synthesis Example 4.

$n_D^{18}$ 1.5778

$\nu_{max}^{film}$ (cm$^{-1}$): 1595, 1505, 1265, 1230, 1115, 1025, 835, 700, $\delta CCl_4$ (ppm): 0.65 (t, J=7.8 Hz, 3H), 1.26 (s, 3H), 1.5–1.9 (m, 2H), 3.30 (s, 2H), 4.28 (s, 2H), 6.6–7.3 (m, 13H).

Elementary Analysis Values as $C_{24}H_{25}ClO_2$: Calculated: C=75.68%, H=6.62%, Cl=9.31% Found: C=75.70%, H=6.58%, Cl=9.27%

SYNTHESIS EXAMPLE 15

3-Phenoxybenzyl 2-(4-fluorophenyl)-2-methylpropyl ether was synthesized according to the procedures described in Synthesis Example 3.

SYNTHESIS EXAMPLE 16

3-Phenoxybenzyl 2-(3,4-dichlorophenyl)-2-ethylpropyl ether was synthesized according to the procedures described in Synthesis Example 1.

SYNTHESIS EXAMPLE 17

3-Phenoxybenzyl 2-(4-methylphenyl)-2-ethylpropyl ether was synthesized according to the procedures described in Synthesis Example 2.

SYNTHESIS EXAMPLE 18

Preparation of 3-phenoxybenzyl 2-(4-formylphenyl)-2-methylpropyl ether is described To 30 ml of dry ether was added 0.70 g of lithium aluminum hydride, and 1.63 g of ethyl acetate was added dropwise to the mixture at 0° C. over a period of 15 minutes. The mixture was allowed to stand at 0° C. for 30 minutes. Then, a solution of 6.0 g of 3-phenoxybenzyl 2-(4-cyanophenyl)-2-methylpropyl ether in 10 ml of dry ether was added dropwise to the mixture, and the resulting mixture was stirred at 0° C. for 1 hour. Then, 20 ml of 4N $H_2SO_4$ was added to the mixture and the resulting mixture was stirred for 30 minutes. The ether layer was separated, washed with water, dried over $Na_2SO_4$, and evaporated.

Then, 6.4 g of the residue was purified by column chromatography on 130 g of silica gel (benzene was used as eluent) to give 2.9 g of starting 3-phenoxybenzyl 2-(4-cyanophenyl)-2-methylpropyl ether and 2.3 g of desired 3-phenoxybenzyl 2-(4-formylphenyl)-2-methylpropyl ether.

$n_D^{20.0}$ 1.5858

$\nu_{max}^{film}$ (cm$^{-1}$): 1720, 1615, 1590, 1500, 1260, 1225, 1105, 835, 700, $\delta_{TMS}^{CCl_4}$ (ppm): 1.37 (s, 6H), 3.40 (s, 2H), 4.37 (s, 2H), 6.7–7.7 (m, 13H), 9.82 (s, 1H)

SYNTHESIS EXAMPLE 19

3-Phenoxybenzyl 2-(4-ethoxymethoxyphenyl)-2-methylpropyl ether was synthesized according to the following procedures.

(1) In 20 ml of wet chloroform was dissolved 1.2 g of 3-phenoxybenzyl 2-(4-formylphenyl)-2-methylpropyl ether, and 0.70 g of m-chloroperbenzoic acid was added to the solution and the mixture was allowed to stand at room temperature for 4 days. The formed precipitate was removed by filtration, and the chloroform layer was washed with dilute alkali and then with water and dried over $Na_2SO_4$, and evaporated under reduced pressure to give 1.0 g of the desired ester. Then, 1.0 g of the ester was dissolved in 30 ml of 5% KOH/methanol and the solution was heated at 50° C. for 3 hours to effect hydrolysis.

Methanol was removed by distillation under reduced pressure, and water and benzene were added to the residue, the pH value of the mixture was reduced below 4 with concd. hydrochloric acid and the mixture was stirred. The mixture was allowed to stand still, and the benzene layer was separated, washed with water, dried over $Na_2SO_4$, and evaporated under reduced pressure to give 0.90 g of a crude ether. The crude ether was purified by column chromatography on 20 g of silica gel (20:1 mixed solvent of benzene and ether was used as eluent) to give 0.60 g of 3-phenoxybenzyl 2-(4-hydroxyphenyl)-2-methylpropyl ether.

$\delta_{TMS}^{CCl_4}$ (ppm): 1.26 (s, 6H), 3.33 (s, 2H), 4.34 (s, 2H), 5.76 (s, 1H), 6.4–7.4 (m, 13H)

(2) To 50 ml dry tetrahydrofuran was added 1.0 g of sodium hydride (60% in oil) and then 5.0 g of 3-phenoxybenzyl 2-(4-hydroxyphenyl)-2-methylpropyl ether in 15 ml of dry tetrahydrofuran was added dropwise to the mixture under reflux over a period of 30 minutes. The mixture was further refluxed for 10 minutes and 5.0 ml of ethyl chloromethyl ether was added dropwise to the mixture for 30 minutes. And the resulting mixture was further refluxed for 10 minutes, cooled to room temperature, poured into water, and extracted with benzene. The benzene extract was washed with water, dried over $Na_2SO_4$, and evaporated to give the oily residue which was purified by column chromatography on 150 g silica gel (20:1 mixed solvent of benzene and ether was used as eluent) to give 5.0 g of 3-phenoxybenzyl 2-(4-ethoxymethoxyphenyl)-2-methylpropyl ether.

$n_D^{20.0}$ 1.5330, $\nu_{max}^{film}$ (cm$^{-1}$): 1580, 1510, 1485, 1230, 1225, 1215, 1105, 1080, 1005, 830, 685, $\delta_{TMS}^{CCl_4}$ (ppm): 1.20 (t, J=7.2 Hz, 3H), 1.30 (s,6H), 3.33 (s,2H), 3.65 (q, J=7.2 Hz, 2H), 4.38 (s, 2H), 5.08 (s, 2H), 6.5–7.4 (m,13H).

SYNTHESIS EXAMPLE 20

3-Phenoxybenzyl 2-(4-methoxymethoxyphenyl)-2-methylpropyl ether was synthesized according to the procedures described in Synthesis Example 19-(2).

$n_D^{20.2}$ 1.5593

$\delta_{TMS}^{CCl_4}$ (ppm): 1.29 (s, 6H), 3.32 (s, 2H), 3.39 (s, 3H), 4.37 (s,2H), 5.03 (s,2H), 6.7–7.4 (m,13H).

SYNTHESIS EXAMPLE 21

3-Phenoxybenzyl 2-(4-cyanophenyl)-2-methylpropyl ether was synthesized according to the procedures described in Synthesis Example 3.

$n_D^{20.4}$ 1.5802

$\nu_{max}^{film}$ (cm$^{-1}$): 2965, 2870, 2235, 1596, 1496, 1260, 1220, 1105, 845, 695, $\delta CCl_4$ (ppm): 1.35 (s, 6H), 3.39 (s, 2H), 4.39 (s, 2H), 6.7–7.5 (m, 13H).

SYNTHESIS EXAMPLE 22

3-Phenoxybenzyl 2-(4-ethoxycarbonylphenyl)-2-methylpropyl ether was synthesized according to the following procedures. (1) A mixture of 3.5 g of 3-phenoxybenzyl 2-(4-cyanophenyl)-2-methylpropyl ether, 7.0 g of potassium hydroxide, 7.0 g of water and 20 ml of ethylene glycol was stirred at 130° C. for 4.0 hours. The mixture was cooled to room temperature, and water was added and the mixture was made acidic by addition of hydrochloric acid. Then, the mixture was extracted with ether, and the ether extract was washed with water, dried over $Na_2SO_4$, and evaporated to give 3.1 g of 3-phenoxybenzyl 2-(carboxyphenyl)-2-methylpropyl ether (mp. 98.5°–102.5° C.).

(2) A mixture of 1.0 g of 3-phenoxybenzyl 2-(4-carboxyphenyl)-2-methylpropyl ether, 0.6 g of phosphorus pentachloride and 15 ml of benzene was treated at 70° to 80° C. for 30 minutes, and the solvent was removed by distillation under reduced pressure. The obtained crude acid chloride was dissolved in 10 ml of benzene and the solution was added dropwise to a mixed solution of 5 ml of ethanol, 1 ml of pyridine and 30 ml of benzene at room temperature. The mixture was allowed to stand for 30 minutes, washed with water and dried over $Na_2SO_4$, and evaporated under reduced pressure to give 1.3 g of a crude ester. The obtained crude ester was purified by column chromatography on 40 g of silica gel (benzene was used as eluent) to give 0.9 g of 3-phenoxybenzyl 2-(4-ethoxycarbonylphenyl)-2-methylpropyl ether.

$\nu_{max}^{film}$ (cm$^{-1}$): 1735, 1620, 1595, 1500, 1380, 1285, 1260, 1225, 1120, $\delta_{TMS}^{CCl_4}$ (ppm): 1.24–1.47 (m, 9H), 3.38 (s, 2H), 4.15–4.41 (m, 4H), 6.7–8.0 (m, 13H).

SYNTHESIS EXAMPLE 23

3-Phenoxybenzyl 2-[4-(2,2,2-trifluoroethoxycarbonyl)-phenyl]-2-methylpropyl ether was synthesized according to the procedures described in Synthesis Example 22-(2).

3-Phenoxybenzyl 2-[4-(2-chloroethoxy)phenyl]-2-methylpropyl ether was obtained by reacting 3-phenoxybenzyl 2-(4-hydroxyphenyl)-2-methylpropyl ether with 1,2-dichloroethane according to conventional procedures.

3-Phenoxybenzyl 2-[4-(1-chlorovinyl)phenyl]-2-methylpropyl ether was obtained by alkali-treating a product obtained by treating 3-phenoxybenzyl 2-(4-acetylphenyl)-2-methylpropyl ether with phosphorus pentachloride.

Typical instances of the compounds included in the scope of the present invention are shown in Table 1.

TABLE 1

| Compound No. | Substituents in General Formula [I] | | | | Etherification Process | Yield (%) | Physical Property Values |
|---|---|---|---|---|---|---|---|
| | Ar | R | Y | B | | | |
| 1 | CH$_3$O—⌬— | CH$_3$— | —O— | —⌬—O—⌬ | A | 61 | $n_D^{18.5}$ 1.5779<br>$C_{24}H_{26}O_3$<br>Calculated (%) / Found (%)<br>C: 79.53 / 79.57<br>H: 7.23 / 7.20 |
| 2 | F—⌬— | $C_2H_5$— | —O— | —⌬—O—⌬—F | D | 46 | $n_D^{20}$ 1.5478<br>$C_{24}H_{24}F_2O_2$<br>Calculated (%) / Found (%)<br>C: 75.37 / 75.54<br>H: 6.32 / 6.21<br>F: 9.94 / 10.01 |
| 3 | CH$_3$—⌬— | CH$_3$— | —O— | —⌬—O—⌬—F | E | 83 | $n_D^{20}$ 1.5563<br>$C_{24}H_{25}FO_2$<br>Calculated (%) / Found (%)<br>C: 79.09 / 79.14<br>H: 6.92 / 6.95<br>F: 5.21 / 5.18 |
| 4 | Cl—⌬— | CH$_3$— | —O— | —⌬—O—⌬—Br | B | 76 | $n_D^{19.8}$ 1.5968<br>$C_{23}H_{22}BrClO_2$<br>Calculated (%) / Found (%)<br>C: 61.97 / 61.82<br>H: 4.98 / 4.91<br>Br: 17.93 / 18.03<br>Cl: 7.95 / 8.05 |
| 5 | ⌬— | CH$_3$— | —O— | —⌬—O—⌬ | D | 52 | $n_D^{18.3}$ 1.5789<br>$C_{23}H_{24}O_2$<br>Calculated (%) / Found (%)<br>C: 83.10 / 83.24<br>H: 7.28 / 7.22 |

TABLE 1-continued

| Compound No. | Substituents in General Formula [I] | | | | Etherification Process | Yield (%) | Physical Property Values |
|---|---|---|---|---|---|---|---|
| | Ar | R | Y | B | | | |
| 6 | 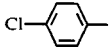 | CH$_3$— | —O— | 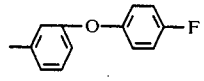 | C | 82 | $n_D^{20}$ 1.5680<br>C$_{23}$H$_{22}$ClFO$_2$<br>Calculated Found<br>(%) (%)<br>C: 71.78 71.67<br>H: 5.76 5.82<br>Cl: 9.21 9.41<br>F: 4.94 4.85 |
| 7 | 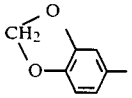 | CH$_3$— | —O— | 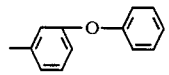 | B | 73 | $n_D^{20.7}$ 1.5839<br>C$_{24}$H$_{24}$O$_4$<br>Calculated Found<br>(%) (%)<br>C: 76.57 76.69<br>H: 6.43 6.35 |
| 8 | 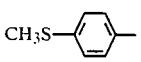 | CH$_3$— | —O— | 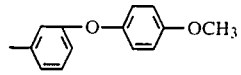 | C | 78 | $n_D^{20}$ 1.5951<br>C$_{25}$H$_{28}$O$_3$S<br>Calculated Found<br>(%) (%)<br>C: 73.50 74.41<br>H: 6.91 6.86<br>S: 7.85 7.92 |
| 9 | 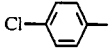 | CH$_3$— | —S— | 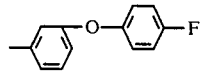 | E | 77 | $n_D^{19.6}$ 1.5947<br>C$_{23}$H$_{22}$ClFOS<br>Calculated Found<br>(%) (%)<br>C: 68.90 69.05<br>H: 5.53 5.44<br>Cl: 8.84 8.89<br>F: 4.74 4.67<br>S: 8.00 8.06 |
| 10 | 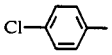 | CH$_3$— | —O— | 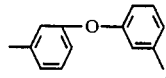 | F | 80 | $n_D^{20.1}$ 1.5840<br>C$_{23}$H$_{22}$Cl$_2$O$_2$<br>Calculated Found<br>(%) (%)<br>C: 68.83 69.01<br>H: 5.53 5.45<br>Cl: 17.67 17.78 |
| 11 | 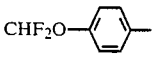 | CH$_3$— | —O— | 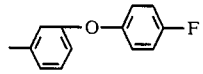 | C | 83 | $n_D^{20}$ 1.5382<br>C$_{24}$H$_{23}$F$_3$O$_3$<br>Calculated Found<br>(%) (%)<br>C: 69.22 69.45<br>H: 5.57 5.43<br>F: 13.69 13.58 |
| 12 | 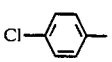 | CH$_3$— | —O— | 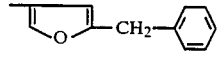 | B | 71 | $n_D^{20}$ 1.5626<br>C$_{22}$H$_{23}$ClO$_2$<br>Calculated Found<br>(%) (%)<br>C: 74.46 74.57<br>H: 6.53 6.62<br>Cl: 9.99 9.86 |
| 13 |  | CH$_3$— | —O— | 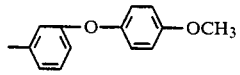 | E | 84 | $n_D^{20}$ 1.5761<br>C$_{24}$H$_{26}$O$_3$<br>Calculated Found<br>(%) (%)<br>C: 79.53 79.76<br>H: 7.23 7.11 |

TABLE 1-continued

| Compound No. | Substituents in General Formula [I] Ar | R | Y | B | Etherification Process | Yield (%) | Physical Property Values |
|---|---|---|---|---|---|---|---|
| 14 | 4-Cl-C₆H₄- | CH₃- | -O- | (3-phenoxy)-2-F-phenyl | A | 76 | $n_D^{20}$ 1.5697<br>$C_{23}H_{22}ClFO_2$<br>Calculated / Found (%)<br>C: 71.78 / 71.92<br>H: 5.76 / 5.68<br>Cl: 9.21 / 9.33<br>F: 4.94 / 4.85 |
| 15 | 4-Cl-C₆H₄- | CH₃- | -O- | 3-(phenylthio)phenyl | F | 77 | $n_D^{20}$ 1.6067<br>$C_{23}H_{23}ClOS$<br>Calculated / Found (%)<br>C: 72.14 / 72.31<br>H: 6.05 / 5.94<br>Cl: 9.26 / 9.38<br>S: 8.37 / 8.43 |
| 16 | 4-F-C₆H₄- | C₂H₅- | -O- | 3-(4-bromophenoxy)phenyl | B | 76 | $n_D^{20.2}$ 1.5778<br>$C_{24}H_{24}BrFO_2$<br>Calculated / Found (%)<br>C: 65.02 / 65.34<br>H: 5.46 / 5.33<br>Br: 18.02 / 18.21<br>F: 4.29 / 4.17 |
| 17 | 3,4-Cl₂-C₆H₃- | CH₃- | -O- | 3-(4-fluorophenoxy)phenyl | B | 74 | $n_D^{20}$ 1.5732<br>$C_{23}H_{21}Cl_2FO_2$<br>Calculated / Found (%)<br>C: 69.09 / 68.88<br>H: 5.29 / 5.34<br>Cl: 8.87 / 8.75<br>F: 4.75 / 4.57 |
| 18 | 4-CHF₂O-C₆H₄- | CH₃- | -O- | 3-phenoxyphenyl | E | 81 | $n_D^{20.5}$ 1.5490<br>$C_{24}H_{24}F_2O_3$<br>Calculated / Found (%)<br>C: 72.35 / 72.46<br>H: 6.07 / 6.01<br>F: 9.54 / 9.63 |
| 19 | 4-Cl-C₆H₄- | CH₃- | -O- | 3-(4-methylphenoxy)phenyl | C | 80 | $n_D^{20}$ 1.5741<br>$C_{24}H_{25}ClO_2$<br>Calculated / Found (%)<br>C: 75.68 / 75.86<br>H: 6.61 / 6.42<br>Cl: 9.31 / 9.22 |
| 20 | 4-Cl-C₆H₄- | CH₃- | -S- | 3-phenoxyphenyl | B | 56 | $n_D^{19.7}$ 1.6074<br>$C_{23}H_{23}ClOS$<br>Calculated / Found (%)<br>C: 72.14 / 71.73<br>H: 6.05 / 6.01<br>Cl: 9.26 / 10.07<br>S: 8.37 / 8.46 |
| 21 | 3,4-Cl₂-C₆H₃- | CH₃- | -O- | 3-(4-bromophenoxy)phenyl | A | 65 | $n_D^{19.5}$ 1.6002<br>$C_{23}H_{21}BrCl_2O_2$<br>Calculated / Found (%)<br>C: 57.52 / 57.43<br>H: 4.41 / 4.29<br>Br: 16.64 / 16.75<br>Cl: 14.76 / 14.58 |

TABLE 1-continued

| Compound No. | Substituents in General Formula [I] Ar | R | Y | B | Etherification Process | Yield (%) | Physical Property Values |
|---|---|---|---|---|---|---|---|
| 22 | 4-Cl-C₆H₄- | CH₃- | -O- | 3-(C₆H₅-CO)-C₆H₄- | E | 79 | $n_D^{20}$ 1.5943<br>C₂₄H₂₃ClO₂<br>Calculated (%) / Found (%)<br>C: 76.08 / 76.21<br>H: 6.12 / 6.03<br>Cl: 9.36 / 9.47 |
| 23 | 3-CF₃-C₆H₄- | CH₃- | -O- | 3-(4-F-C₆H₄-O)-C₆H₄- | F | 84 | $n_D^{19.6}$ 1.5293<br>C₂₄H₂₂F₄O₂<br>Calculated (%) / Found (%)<br>C: 68.89 / 68.93<br>H: 5.30 / 5.35<br>F: 18.16 / 18.02 |
| 24 | 4-CH₃S-C₆H₄- | CH₃- | -O- | 3-phenoxyphenyl | B | 70 | $n_D^{19.8}$ 1.5921<br>C₂₄H₂₆O₂S<br>Calculated (%) / Found (%)<br>C: 76.15 / 76.34<br>H: 6.92 / 7.01<br>S: 8.47 / 8.39 |
| 25 | 4-CHF₂O-C₆H₄- | CH₃- | -O- | 3-(3-Cl-C₆H₄-O)-C₆H₄- | A | 63 | $n_D^{19.9}$ 1.5580<br>C₂₄H₂₃ClF₂O₃<br>Calculated (%) / Found (%)<br>C: 66.59 / 66.74<br>H: 5.35 / 5.28<br>Cl: 8.19 / 8.31<br>F: 8.78 / 8.70 |
| 26 | 4-Cl-C₆H₄- | CH₃- | -O- | 3-(3-CH₃-C₆H₄-O)-C₆H₄- | C | 83 | $n_D^{20}$ 1.5774<br>C₂₄H₂₅ClO₂<br>Calculated (%) / Found (%)<br>C: 75.68 / 75.81<br>H: 6.61 / 6.53<br>Cl: 9.31 / 9.54 |
| 27 | 4-CH₃O-C₆H₄- | CH₃- | -O- | 3-(4-CH₃O-C₆H₄-O)-C₆H₄- | E | 80 | $n_D^{20}$ 1.5724<br>C₂₅H₂₈O₄<br>Calculated (%) / Found (%)<br>C: 76.50 / 76.74<br>H: 7.19 / 7.08 |
| 28 | C₆H₅- | CH₃- | -O- | 3-(4-F-C₆H₄-O)-C₆H₄- | B | 77 | $n_D^{20}$ 1.5638<br>C₂₃H₂₃FO₂<br>Calculated (%) / Found (%)<br>C: 78.83 / 78.99<br>H: 6.62 / 6.45<br>F: 5.42 / 5.37 |
| 29 | 3-CH₃-C₆H₄- | C₂H₅- | -O- | 3-(3-Cl-C₆H₄-O)-C₆H₄- | C | 85 | $n_D^{20.1}$ 1.5750<br>C₂₅H₂₇ClO₂<br>Calculated (%) / Found (%)<br>C: 76.03 / 76.25<br>H: 6.89 / 6.72<br>Cl: 8.98 / 9.09 |

TABLE 1-continued

| Compound No. | Substituents in General Formula [1] | | | | Etherification Process | Yield (%) | Physical Property Values |
|---|---|---|---|---|---|---|---|
| | Ar | R | Y | B | | | |
| 30 | 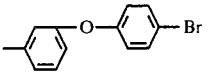 CHF₂O—⟨⟩— | CH₃— | —O— | 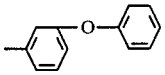 —⟨⟩—O—⟨⟩—Br | B | 78 | $n_D^{20.2}$ 1.5648<br>$C_{24}H_{23}BrF_2O_3$<br>Calculated  Found<br>(%)  (%)<br>C: 60.39  60.52<br>H: 4.86  4.75<br>Br: 16.74  16.87<br>F: 7.96  7.83 |
| 31 | 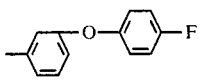 | CH₃— | —O— | —⟨⟩—O—⟨⟩ | E | 78 | $n_D^{20.1}$ 1.6138<br>$C_{27}H_{26}O_2$<br>Calculated  Found<br>(%)  (%)<br>C: 84.78  84.89<br>H: 6.85  6.76 |
| 32 | CH₃O—⟨⟩— | CH₃— | —O— | —⟨⟩—O—⟨⟩—F | F | 77 | $n_D^{20}$ 1.5637<br>$C_{24}H_{25}FO_3$<br>Calculated  Found<br>(%)  (%)<br>C: 75.77  75.86<br>H: 6.62  6.49<br>F: 4.99  4.91 |
| 33 | CH₃—⟨⟩— | CH₃— | —O— | —⟨⟩—O—⟨⟩—Br | C | 81 | $n_D^{20.2}$ 1.5838<br>$C_{24}H_{25}BrO_2$<br>Calculated  Found<br>(%)  (%)<br>C: 67.77  67.84<br>H: 5.92  5.85<br>Br: 18.79  18.89 |
| 34 | Cl—⟨⟩— | CH₃— | —O— | —⟨⟩—O—⟨⟩—OCH₃ | E | 82 | $n_D^{20}$ 1.5758<br>$C_{24}H_{25}ClO_3$<br>Calculated  Found<br>(%)  (%)<br>C: 72.63  72.87<br>H: 6.35  6.14<br>Cl: 8.93  9.01 |
| 35 | Cl—⟨⟩— | CH₃— | —O— | —⟨⟩—CH₂—⟨⟩ | B | 63 | $n_D^{20}$ 1.5771<br>$C_{24}H_{25}ClO$<br>Calculated  Found<br>(%)  (%)<br>C: 78.99  79.13<br>H: 6.91  6.79<br>Cl: 9.72  9.85 |
| 36 | 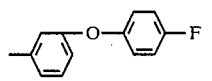 CH₃ on ring | CH₃— | —O— | —⟨⟩—O—⟨⟩—F | C | 84 | $n_D^{20}$ 1.5598<br>$C_{24}H_{25}FO_2$<br>Calculated  Found<br>(%)  (%)<br>C: 79.09  79.32<br>H: 6.92  6.71<br>F: 5.21  5.16 |
| 37 | Cl—⟨⟩— | CH₃— | —S— | —⟨⟩—O—⟨⟩—Br | C | 75 | $n_D^{20.1}$ 1.6065<br>$C_{23}H_{22}BrClOS$<br>Calculated  Found<br>(%)  (%)<br>C: 59.81  59.94<br>H: 4.80  4.69<br>Br: 17.30  17.51<br>Cl: 7.68  7.75<br>S: 6.94  6.82 |

TABLE 1-continued

| Compound No. | Substituents in General Formula [I] Ar | R | Y | B | Etherification Process | Yield (%) | Physical Property Values |
|---|---|---|---|---|---|---|---|
| 38 | 3,4-dichlorophenyl | CH$_3$— | —O— | 3-chlorophenoxyphenyl | E | 81 | $n_D^{22.0}$ 1.5912<br>C$_{23}$H$_{21}$Cl$_3$O$_2$<br>Calculated Found<br>(%) (%)<br>C: 63.39 63.52<br>H: 4.86 4.73<br>Cl: 24.41 24.66 |
| 39 | 3-CF$_3$-phenyl | CH$_3$— | —O— | phenoxyphenyl | F | 80 | $n_D^{20.0}$ 1.5375<br>C$_{24}$H$_{23}$F$_3$O$_2$<br>Calculated Found<br>(%) (%)<br>C: 71.99 72.14<br>H: 5.79 5.71<br>F: 14.23 14.29 |
| 40 | 4-Br-phenyl | CH$_3$— | —O— | 4-methoxyphenoxyphenyl | B | 73 | $n_D^{20}$ 1.5875<br>C$_{24}$H$_{25}$BrO$_3$<br>Calculated Found<br>(%) (%)<br>C: 65.31 65.52<br>H: 5.71 5.65<br>Br: 18.10 18.28 |
| 41 | 3,4-dichlorophenyl | CH$_3$— | —O— | 4-methoxyphenoxyphenyl | F | 78 | $n_D^{20}$ 1.5830<br>C$_{24}$H$_{24}$Cl$_2$O$_3$<br>Calculated Found<br>(%) (%)<br>C: 66.83 66.72<br>H: 5.61 5.38<br>Cl: 16.43 16.62 |
| 42 | 3-CF$_3$-phenyl | CH$_3$— | —O— | 4-bromophenoxyphenyl | E | 79 | $n_D^{20.0}$ 1.5538<br>C$_{24}$H$_{22}$BrF$_3$O$_2$<br>Calculated Found<br>(%) (%)<br>C: 60.14 60.26<br>H: 4.63 4.52<br>Br: 16.67 16.79<br>F: 11.89 11.75 |
| 43 | 4-NO$_2$-phenyl | CH$_3$— | —O— | phenoxyphenyl | C | 82 | $n_D^{20}$ 1.5885<br>C$_{23}$H$_{23}$NO$_4$<br>Calculated Found<br>(%) (%)<br>C: 73.19 73.34<br>H: 6.14 6.02<br>N: 3.71 3.89 |
| 44 | 4-CH$_3$-phenyl | CH$_3$— | —O— | 4-methoxyphenoxyphenyl | A | 59 | $n_D^{20}$ 1.5707<br>C$_{25}$H$_{28}$O$_3$<br>Calculated Found<br>(%) (%)<br>C: 79.75 79.99<br>H: 7.50 7.48 |
| 45 | 4-F-phenyl | CH$_3$— | —O— | 4-fluorophenoxyphenyl | F | 84 | $n_D^{20}$ 1.5532<br>C$_{23}$H$_{22}$F$_2$O$_2$<br>Calculated Found<br>(%) (%)<br>C: 74.98 74.79<br>H: 6.02 5.95<br>F: 10.31 10.41 |

TABLE 1-continued

| Compound No. | Substituents in General Formula [1] Ar | R | Y | B | Etherification Process | Yield (%) | Physical Property Values |
|---|---|---|---|---|---|---|---|
| 46 | 4-Cl-C6H4- | C2H5- | -O- | -C6H4-O-C6H4-Br | A | 68 | $n_D^{19.8}$ 1.5912<br>$C_{24}H_{24}BrClO_2$<br>Calculated / Found (%)<br>C: 62.69 / 62.93<br>H: 5.26 / 5.17<br>Br: 17.38 / 17.51<br>Cl: 7.71 / 7.58 |
| 47 | 4-CH3-C6H4- | CH3- | -O- | -C6H4-O-C6H5 | A | 64 | $n_D^{18.5}$ 1.5794<br>$C_{24}H_{26}O_2$<br>Calculated / Found (%)<br>C: 83.20 / 83.25<br>H: 7.56 / 7.59 |
| 48 | 3,4-Cl2-C6H3- | CH3- | -O- | -C6H4-O-C6H5 | B | 78 | $n_D^{18}$ 1.5890<br>$C_{23}H_{22}Cl_2O_2$<br>Calculated / Found (%)<br>C: 68.83 / 68.78<br>H: 5.53 / 5.48<br>Cl: 16.67 / 16.72 |
| 49 | 4-Cl-C6H4- | CH3- | -O- | -C6H4-O-C6H5 | C | 74 | $n_D^{17}$ 1.5832<br>$C_{23}H_{23}ClO_2$<br>Calculated / Found (%)<br>C: 75.30 / 75.18<br>H: 6.32 / 6.51<br>Cl: 9.66 / 9.70 |
| 50 | 4-Cl-C6H4- | C2H5- | -O- | -C6H4-O-C6H5 | D | 48 | $n_D^{18}$ 1.5778<br>$C_{24}H_{25}ClO_2$<br>Calculated / Found (%)<br>C: 75.68 / 75.70<br>H: 6.62 / 6.58<br>Cl: 9.31 / 9.27 |
| 51 | 4-F-C6H4- | CH3- | -O- | -C6H4-O-C6H5 | C | 80 | $n_D^{19.9}$ 1.5695<br>$C_{23}H_{23}FO_2$<br>Calculated / Found (%)<br>C: 78.83 / 78.91<br>H: 6.62 / 6.68<br>F: 5.43 / 5.35 |
| 52 | 3,4-Cl2-C6H3- | C2H5- | -O- | -C6H4-O-C6H5 | A | 75 | $n_D^{18}$ 1.5828<br>$C_{24}H_{24}Cl_2O_2$<br>Calculated / Found (%)<br>C: 69.40 / 69.45<br>H: 5.82 / 5.76<br>Cl: 17.07 / 17.00 |
| 53 | 4-CH3-C6H4- | C2H5- | -O- | -C6H4-O-C6H5 | B | 73 | $n_D^{18}$ 1.5790<br>$C_{25}H_{28}O_2$<br>Calculated / Found (%)<br>C: 83.29 / 83.34<br>H: 7.83 / 7.88 |

TABLE 1-continued

| Compound No. | Ar | R | Y | B | Etherification Process | Yield (%) | Physical Property Values |
|---|---|---|---|---|---|---|---|
| 54 | NC—C₆H₄— | CH₃— | —O— | —C₆H₄—O—C₆H₅ | C | 86 | $n_D^{20.4}$ 1.5802<br>$C_{24}H_{23}NO_2$<br>Calculated (%) / Found (%)<br>C: 80.64 / 80.38<br>H: 6.48 / 6.35<br>N: 3.92 / 4.03 |
| 55 | C₂H₅O—C₆H₄— | CH₃— | —O— | —C₆H₄—O—C₆H₅ | B | 77 | $n_D^{20.2}$ 1.5732<br>$C_{25}H_{28}O_3$<br>Calculated (%) / Found (%)<br>C: 79.76 / 79.97<br>H: 7.50 / 7.34 |
| 56 | 3,5-Cl₂-C₆H₃— | CH₃— | —O— | —C₆H₄—O—C₆H₅ | F | 84 | $n_D^{20.0}$ 1.5882<br>$C_{23}H_{22}Cl_2O_2$<br>Calculated (%) / Found (%)<br>C: 71.69 / 71.85<br>H: 5.76 / 5.48<br>Cl: 18.40 / 18.65 |
| 57 | n-C₃H₇O—C₆H₄— | CH₃— | —O— | —C₆H₄—O—C₆H₅ | E | 82 | $n_D^{18.8}$ 1.5678<br>$C_{26}H_{30}O_3$<br>Calculated (%) / Found (%)<br>C: 79.97 / 80.16<br>H: 7.74 / 7.52 |
| 58 | 3-Cl-4-F-C₆H₃— | CH₃— | —O— | —C₆H₄—O—C₆H₄—F | D | 51 | $n_D^{20.2}$ 1.5672<br>$C_{23}H_{21}ClF_2O_2$<br>Calculated (%) / Found (%)<br>C: 68.57 / 68.81<br>H: 5.25 / 5.39<br>Cl: 8.80 / 8.95<br>F: 9.43 / 9.31 |
| 59 | (CH₃)₂CHO—C₆H₄— | CH₃— | —O— | —C₆H₄—O—C₆H₅ | C | 80 | $n_D^{18.6}$ 1.5680<br>$C_{26}H_{30}O_3$<br>Calculated (%) / Found (%)<br>C: 79.97 / 79.79<br>H: 7.74 / 7.91 |
| 60 | CH₃CO—C₆H₄— | CH₃— | —O— | —C₆H₄—O—C₆H₅ | B | 75 | $n_D^{20.3}$ 1.5815<br>$C_{25}H_{26}O_3$<br>Calculated (%) / Found (%)<br>C: 80.18 / 80.32<br>H: 7.00 / 6.88 |
| 61 | cyclo-C₅H₉O—C₆H₄— | CH₃— | —O— | —C₆H₄—O—C₆H₅ | E | 85 | $n_D^{20.1}$ 1.5753<br>$C_{28}H_{32}O_3$<br>Calculated (%) / Found (%)<br>C: 80.73 / 80.55<br>H: 7.74 / 7.89 |
| 62 | n-C₅H₁₁O—C₆H₄— | CH₃— | —O— | —C₆H₄—O—C₆H₅ | A | 64 | $n_D^{19.8}$ 1.5572<br>$C_{28}H_{34}O_3$<br>Calculated (%) / Found (%)<br>C: 80.35 / 80.26<br>H: 8.19 / 8.31 |

TABLE 1-continued

| Compound No. | Substituents in General Formula [I] Ar | R | Y | B | Etherification Process | Yield (%) | Physical Property Values |
|---|---|---|---|---|---|---|---|
| 63 | (CH₃)₂CH—C₆H₄— | CH₃— | —O— | —C₆H₃(—O—C₆H₅)— | F | 81 | $n_D^{20.2}$ 1.5683<br>$C_{26}H_{30}O_2$<br>Calculated (%) / Found (%)<br>C: 83.38  83.19<br>H: 8.07  7.89 |
| 64 | (CH₃)₂CH—CH₂O—C₆H₄— | CH₃— | —O— | —C₆H₃(—O—C₆H₅)— | E | 85 | $n_D^{19.7}$ 1.5590<br>$C_{27}H_{32}O_3$<br>Calculated (%) / Found (%)<br>C: 80.16  80.01<br>H: 7.97  8.12 |
| 65 | I—C₆H₄— | CH₃— | —O— | —C₆H₃(—O—C₆H₅)— | D | 59 | $n_D^{19.7}$ 1.5996<br>$C_{23}H_{23}IO_2$<br>Calculated (%) / Found (%)<br>C: 58.24  58.52<br>H: 4.89  5.03<br>I: 26.76  26.48 |
| 66 | C₂H₅O—C₆H₄— | CH₃— | —O— | —C₆H₃(—O—C₆H₄—Br)— | A | 75 | $n_D^{19.9}$ 1.5828<br>$C_{25}H_{27}BrO_3$<br>Calculated (%) / Found (%)<br>C: 65.94  66.13<br>H: 5.98  6.14<br>Br: 17.55  17.36 |
| 67 | CH₂=CHO—C₆H₄— | CH₃— | —O— | —C₆H₃(—O—C₆H₅)— | C | 84 | $C_{25}H_{26}O_3$<br>Calculated (%) / Found (%)<br>C: 80.18  80.30<br>H: 7.00  6.87<br>δCCl₄(ppm): 1.26(s, 6H), 3.30(s,2H), 4.20–4.72(m,4H), 6.39–6.68(m,1H), 6.7–7.4(m,13H) |
| 68 | C₆H₅—C₆H₄— | CH₃— | —O— | —C₆H₃(—O—C₆H₅)— | F | 82 | $n_D^{19.6}$ 1.6066<br>$C_{29}H_{28}O_2$<br>Calculated (%) / Found (%)<br>C: 85.26  85.44<br>H: 6.91  6.79 |
| 69 | n-C₄H₉O—C₆H₄— | CH₃— | —O— | —C₆H₃(—O—C₆H₅)— | C | 85 | $n_D^{19.1}$ 1.5620<br>$C_{27}H_{32}O_3$<br>Calculated (%) / Found (%)<br>C: 80.16  80.31<br>H: 7.97  8.11 |
| 70 | (CH₃)(C₂H₅)CHO—C₆H₄— | CH₃— | —O— | —C₆H₃(—O—C₆H₅)— | E | 81 | $n_D^{20.0}$ 1.5627<br>$C_{27}H_{32}O_3$<br>Calculated (%) / Found (%)<br>C: 80.16  80.03<br>H: 7.97  7.85 |
| 71 | CH₃-naphthyl- | CH₃— | —O— | —C₆H₃(—O—C₆H₅)— | F | 86 | $n_D^{19.8}$ 1.6082<br>$C_{28}H_{28}O_2$<br>Calculated (%) / Found (%)<br>C: 84.81  84.55<br>H: 7.12  7.24 |

TABLE 1-continued

| Compound No. | Substituents in General Formula [I] | | | | Etherification Process | Yield (%) | Physical Property Values |
|---|---|---|---|---|---|---|---|
| | Ar | R | Y | B | | | |
| 72 | cyclohexyl-O-C₆H₄- | CH₃— | —O— | -C₆H₃(CH₃)-O-C₆H₅ | A | 78 | $n_D^{20.1}$ 1.5516<br>$C_{29}H_{34}O_3$<br>Calculated Found<br>(%) (%)<br>C: 80.89  81.13<br>H: 7.96  7.78 |
| 73 | 2-Cl-4-CH₃-C₆H₃- | CH₃— | —O— | -C₆H₃(CH₃)-O-C₆H₅ | F | 88 | $n_D^{20.0}$ 1.5784<br>$C_{24}H_{25}ClO_2$<br>Calculated Found<br>(%) (%)<br>C: 75.68  75.84<br>H: 6.62  6.41<br>Cl: 9.31  9.53 |
| 74 | ICH₂—CF₂O—C₆H₄- | CH₃— | —O— | -C₆H₃(CH₃)-O-C₆H₅ | A | 74 | $C_{25}H_{25}IF_3O_3$<br>Calculated Found<br>(%) (%)<br>C: 55.77  55.57<br>H: 4.68  4.84<br>F: 7.06  7.21<br>I: 23.57  23.33<br>$\delta CCl_4$(ppm): 1.31(s,6H),<br>3.31(s,2H), 3.7–4.0<br>(m,2H), 4.33(s,2H)<br>6.7–7.5(m,13H) |
| 75 | 2-Cl-3-F-C₆H₃- | CH₃— | —O— | -C₆H₃(CH₃)-O-C₆H₅ | D | 55 | $n_D^{20.3}$ 1.5772<br>$C_{23}H_{22}ClFO_2$<br>Calculated Found<br>(%) (%)<br>C: 71.78  71.55<br>H: 5.76  5.92<br>Cl: 9.21  9.38<br>F: 4.94  4.80 |
| 76 | C₆H₅-O-C₆H₄- | CH₃— | —O— | -C₆H₃(CH₃)-O-C₆H₅ | B | 79 | $n_D^{19.7}$ 1.5930<br>$C_{29}H_{28}O_3$<br>Calculated Found<br>(%) (%)<br>C: 82.05  82.22<br>H: 6.65  6.47 |
| 77 | (CH₃)₂CH-C₆H₄- | CH₃— | —O— | -C₆H₃(CH₃)-O-C₆H₄-F | C | 85 | $n_D^{19.7}$ 1.5772<br>$C_{26}H_{29}FO_2$<br>Calculated Found<br>(%) (%)<br>C: 79.56  79.73<br>H: 7.45  7.26<br>F: 4.84  4.98 |
| 78 | 2-Cl-3-C₂H₅O-C₆H₃- | CH₃— | —O— | -C₆H₃(CH₃)-O-C₆H₅ | F | 86 | $n_D^{19.6}$ 1.5748<br>$C_{25}H_{27}ClO_3$<br>Calculated Found<br>(%) (%)<br>C: 73.07  73.13<br>H: 6.62  6.81<br>Cl: 8.63  8.45 |
| 79 | CH₃—CF₂O—C₆H₄- | CH₃— | —O— | -C₆H₃(CH₃)-O-C₆H₅ | C | 83 | $C_{25}H_{26}F_2O_3$<br>Calculated Found<br>(%) (%)<br>C: 72.80  72.75<br>H: 6.35  6.53<br>F: 9.21  9.02<br>$\delta CCl_4$(ppm): 1.31(s,6H),<br>1.85(t,J=13Hz,3H),<br>3.31(s,2H), 4.33<br>(s,2H), 6.7–7.5(m, |

TABLE 1-continued

| Compound No. | Substituents in General Formula [1] Ar | R | Y | B | Etherification Process | Yield (%) | Physical Property Values |
|---|---|---|---|---|---|---|---|
| | | | | | | | 13H) |
| 80 | CH₃OCH₂—C₆H₄— | CH₃— | —O— | —C₆H₃(O-C₆H₅)— | A | 69 | $n_D^{19.8}$ 1.5630<br>$C_{25}H_{28}O_3$<br>Calculated  Found<br>(%)  (%)<br>C: 79.76  79.49<br>H: 7.50  7.62 |
| 81 | C₂H₅OCH₂O—C₆H₄— | CH₃— | —O— | —C₆H₃(O-C₆H₅)— | | | $n_D^{20.0}$ 1.5330<br>$C_{26}H_{30}O_4$<br>Calculated  Found<br>(%)  (%)<br>C: 76.82  76.58<br>H: 7.44  7.63 |
| 82 | C₂H₅OCH₂—C₆H₄— | CH₃— | —O— | —C₆H₃(O-C₆H₅)— | E | 78 | $n_D^{19.9}$ 1.5632<br>$C_{26}H_{30}O_3$<br>Calculated  Found<br>(%)  (%)<br>C: 79.97  80.11<br>H: 7.74  7.57<br>δCCl₄(ppm): 1.09(t,J=7Hz, 3H), 1.33(s,6H),<br>3.30–3.52(m,4H),<br>4.39(s,4H), 6.7–7.4<br>(m,13H) |
| 83 | CH₃OCH₂O—C₆H₄— | CH₃— | —O— | —C₆H₃(O-C₆H₅)— | | | $n_D^{20.2}$ 1.5593<br>$C_{25}H_{28}O_4$<br>Calculated  Found<br>(%)  (%)<br>C: 76.50  76.77<br>H: 7.19  6.98 |
| 84 | CH₃CH(OC₂H₅)—C₆H₄— | CH₃— | —O— | —C₆H₃(O-C₆H₅)— | C | 84 | $n_D^{20.1}$ 1.5524<br>$C_{27}H_{32}O_3$<br>Calculated  Found<br>(%)  (%)<br>C: 80.16  80.01<br>H: 7.97  8.10 |
| 85 | C₂H₅OC(O)—C₆H₄— | CH₃— | —O— | —C₆H₃(O-C₆H₅)— | | | $n_D^{20.2}$ 1.5660<br>$C_{26}H_{28}O_4$<br>Calculated  Found<br>(%)  (%)<br>C: 77.20  77.03<br>H: 6.98  7.12 |
| 86 | CH₃CH(OCH₃)—C₆H₄— | CH₃— | —O— | —C₆H₃(O-C₆H₅)— | C | 85 | $n_D^{20.0}$ 1.5582<br>$C_{26}H_{30}O_3$<br>Calculated  Found<br>(%)  (%)<br>C: 79.97  79.82<br>H: 7.74  7.62 |
| 87 | CH₂=C(CH₃)—C₆H₄— | CH₃— | —O— | —C₆H₃(O-C₆H₅)— | E | 83 | $n_D^{20.4}$ 1.5830<br>$C_{26}H_{28}O_2$<br>Calculated  Found<br>(%)  (%)<br>C: 83.83  83.79<br>H: 7.58  7.73 |

TABLE 1-continued

| Compound No. | Ar | R | Y | B | Etherification Process | Yield (%) | Physical Property Values |
|---|---|---|---|---|---|---|---|
| 88 | 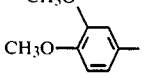 | CH$_3$— | —O— | 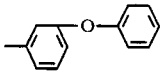 | C | 90 | m.p. 54.6–55.1° C.<br>C$_{25}$H$_{28}$O$_4$<br>Calculated (%) / Found (%)<br>C: 76.50 / 76.68<br>H: 7.19 / 7.32 |
| 89 | 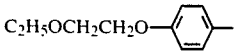 | CH$_3$— | —O— | 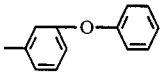 |  |  | $n_D^{19.7}$ 1.5587<br>C$_{27}$H$_{32}$O$_4$<br>Calculated (%) / Found (%)<br>C: 77.11 / 77.34<br>H: 7.67 / 7.49 |
| 90 | 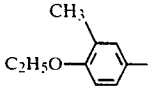 | CH$_3$— | —O— | 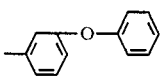 | E | 86 | $n_D^{20.2}$ 1.5688<br>C$_{26}$H$_{30}$O$_3$<br>Calculated (%) / Found (%)<br>C: 79.97 / 80.15<br>H: 7.74 / 7.63 |
| 91 | 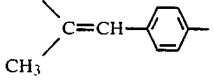 | CH$_3$— | —O— | 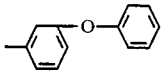 | A | 70 | $n_D^{19.8}$ 1.5812<br>C$_{27}$H$_{30}$O$_2$<br>Calculated (%) / Found (%)<br>C: 83.90 / 84.15<br>H: 7.82 / 7.76 |
| 92 | 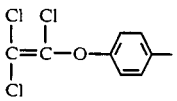 | CH$_3$— | —O— | 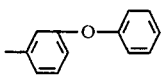 | C | 78 | $n_D^{19.8}$ 1.5832<br>C$_{25}$H$_{23}$Cl$_3$O$_3$<br>Calculated (%) / Found (%)<br>C: 62.85 / 63.09<br>H: 4.85 / 4.70<br>Cl: 22.26 / 22.41 |
| 93 | 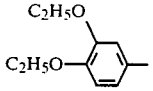 | CH$_3$— | —O— | 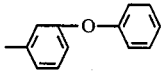 | E | 88 | $n_D^{20.3}$ 1.5537<br>C$_{27}$H$_{32}$O$_4$<br>Calculated (%) / Found (%)<br>C: 77.11 / 77.35<br>H: 7.67 / 7.49 |
| 94 | 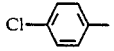 | CH$_3$— | —O— | 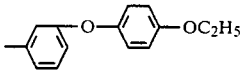 | F | 77 | $n_D^{20.1}$ 1.5749<br>C$_{25}$H$_{27}$ClO$_3$<br>Calculated (%) / Found (%)<br>C: 73.07 / 73.24<br>H: 6.62 / 6.43<br>Cl: 8.63 / 8.86<br>δCCl$_4$(ppm): 1.2–1.5(m,9H), 3.32(s,2H), 3.91(q,2H), 4.36(s,2H), 6.7–7.4(m,12H) |
| 95 | 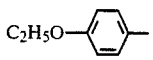 | CH$_3$— | —S— | 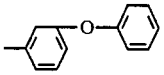 | B | 79 | C$_{25}$H$_{28}$O$_2$S<br>Calculated (%) / Found (%)<br>C: 76.49 / 76.20<br>H: 7.19 / 7.08<br>S: 8.17 / 8.39<br>δCCl$_4$(ppm): 1.2–1.5(m,9H), 2.54(s,2H), 3.31(s,2H), 3.88(q,2H), 6.7–7.4(m,13H) |
| 96 | 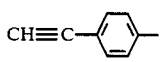 | CH$_3$— | —O— | 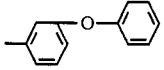 | A | 76 | C$_{25}$H$_{24}$O$_2$<br>Calculated (%) / Found (%)<br>C: 84.24 / 84.07<br>H: 6.79 / 6.95 |

TABLE 1-continued

| Compound No. | Substituents in General Formula [I] | | | | Etherification Process | Yield (%) | Physical Property Values |
|---|---|---|---|---|---|---|---|
| | Ar | | R | Y | B | | | |

| | | | | | | | δCCl₄(ppm): 1.28(s,6H), 3.08(s,1H), 3.34 (s,2H), 4.37(s,2H), 6.7-7.4(m,13H) |
| 97 | 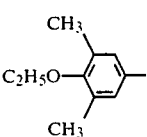 | CH₃— | —O— | 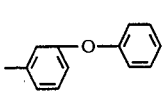 | F | 82 | C₂₇H₃₂O₃<br>Calculated Found<br>(%)　　(%)<br>C: 80.16　80.38<br>H: 7.97　8.15<br>δCCl₄(ppm): 1.2-1.5(m,9H), 2.20(s,6H), 3.32 (s,2H), 3.87(q,2H), 4.34(s,2H), 6.4-7.4(m,11H) |
| 98 | 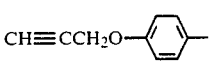 | CH₃— | —O— | 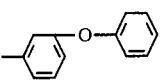 | C | 83 | $n_D^{19.9}$ 1.5775<br>C₂₆H₂₆O₃<br>Calculated Found<br>(%)　　(%)<br>C: 80.80　80.62<br>H: 6.78　6.71 |
| 99 | 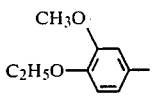 | CH₃— | —O— | 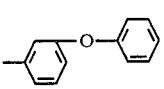 | B | 84 | C₂₆H₃₀O₄<br>Calculated Found<br>(%)　　(%)<br>C: 76.82　76.59<br>H: 7.44　7.56<br>δCCl₄(ppm): 1.2-1.5(m,9H), 3.32(s,2H), 3.68 (d,3H), 3.8-4.1 (m,2H), 4.34(s,2H), 6.5-7.4(m,12H) |
| 100 | 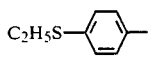 | CH₃— | —O— | 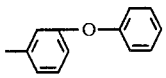 | F | 79 | $n_D^{19.6}$ 1.5940<br>C₂₅H₂₈O₂S<br>Calculated Found<br>(%)　　(%)<br>C: 76.49　76.32<br>H: 7.19　7.34<br>S: 8.17　8.01<br>δCCl₄(ppm): 1.1-1.4(m,9H), 2.79(q,2H), 3.33 (s,2H), 4.36(s,2H), 6.7-7.3(m,13H) |
| 101 | 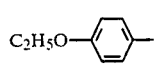 | CH₃— | —O— | 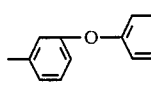 | F | 83 | $n_D^{20.7}$ 1.5762<br>C₂₇H₃₂O₄<br>Calculated Found<br>(%)　　(%)<br>C: 77.11　77.33<br>H: 7.67　7.49<br>δCCl₄(ppm): 1.2-1.5(m,12H), 3.32(s,2H), 3.8-4.1(m,4H), 4.36 (s,2H), 6.6-7.4 (m,12H) |
| 102 | 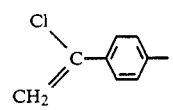 | CH₃— | —O— | 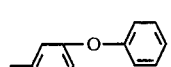 | | | C₂₅H₂₅ClO₂<br>Calculated Found<br>(%)　　(%)<br>C: 76.42　76.60<br>H: 6.41　6.19<br>Cl: 9.02　9.35<br>δCCl₄(ppm): 1.34(s,6H), 3.38(s,2H), 4.41 (s,2H), 5.42(s,1H), 5.62(s,1H), 6.8-7.4(m,13H) |

TABLE 1-continued

| Compound No. | Ar | R | Y | B | Etherification Process | Yield (%) | Physical Property Values |
|---|---|---|---|---|---|---|---|
| 103 | C$_2$H$_5$O—C$_6$H$_4$— | C$_2$H$_5$— | —O— | —C$_6$H$_4$—O—C$_6$H$_5$ | C | 88 | C$_{26}$H$_{30}$O$_2$<br>Calculated / Found (%)<br>C: 79.97 / 79.69<br>H: 7.74 / 7.92<br>$\delta_{TMS}^{CCl_4}$ (ppm): 0.65(t, J=8Hz,3H), 1.2–1.9(m,8H), 3.37 (s,2H), 3.92(q,J=7Hz, 2H), 4.37(s,2H), 6.5–7.4(m,13H) |
| 104 | CF$_3$S—C$_6$H$_4$— | CH$_3$— | —O— | —C$_6$H$_4$—O—C$_6$H$_5$ | A | 81 | C$_{24}$H$_{23}$F$_3$O$_2$S<br>Calculated / Found (%)<br>C: 66.65 / 66.42<br>H: 5.36 / 5.53<br>F: 13.18 / 13.05<br>S: 7.41 / 7.67<br>$\delta$CCl$_4$(ppm): 1.31(s,6H), 3.34(s,2H), 4.38(s,2H), 6.8–7.3(m,13H) |
| 105 | (CH$_3$)$_3$C—C$_6$H$_4$— | CH$_3$— | —O— | —C$_6$H$_4$—O—C$_6$H$_5$ | E | 86 | $n_D^{20.4}$ 1.5607<br>C$_{27}$H$_{32}$O$_2$<br>Calculated / Found (%)<br>C: 83.46 / 83.58<br>H: 8.30 / 8.41 |
| 106 | CF$_3$CH$_2$OC(O)—C$_6$H$_4$— | CH$_3$ | —O— | —C$_6$H$_4$—O—C$_6$H$_5$ | | | $n_D^{19.7}$ 1.5394<br>C$_{26}$H$_{25}$F$_3$O$_4$<br>Calculated / Found (%)<br>C: 68.11 / 68.35<br>H: 5.50 / 5.63<br>F: 12.43 / 12.22 |
| 107 | Br—C$_6$H$_4$— | CH$_3$— | —O— | —C$_6$H$_4$—O—C$_6$H$_5$ | D | 63 | $n_D^{19.8}$ 1.5943<br>C$_{23}$H$_{23}$BrO$_2$<br>Calculated / Found (%)<br>C: 67.16 / 67.42<br>H: 5.64 / 5.71<br>Br: 19.43 / 19.70 |
| 108 | ClCH$_2$CH$_2$O—C$_6$H$_4$— | CH$_3$— | —O— | —C$_6$H$_4$—O—C$_6$H$_5$ | | | $n_D^{20.0}$ 1.5742<br>C$_{25}$H$_{27}$ClO$_3$<br>Calculated / Found (%)<br>C: 73.07 / 72.74<br>H: 6.62 / 6.53<br>Cl: 8.63 / 8.89 |
| 109 | (CH$_3$)$_2$C$_6$H$_3$— | CH$_3$— | —O— | —C$_6$H$_4$—O—C$_6$H$_5$ | C | 82 | $n_D^{19.6}$ 1.5768<br>C$_{25}$H$_{28}$O$_2$<br>Calculated / Found (%)<br>C: 83.30 / 83.14<br>H: 7.83 / 7.98 |
| 110 | CH$_3$CH$_2$C(=CH$_2$)—C$_6$H$_4$— | CH$_3$— | —O— | —C$_6$H$_4$—O—C$_6$H$_5$ | F | 87 | C$_{27}$H$_{30}$O$_2$<br>Calculated / Found (%)<br>C: 83.90 / 83.69<br>H: 7.82 / 7.71<br>$\delta$CCl$_4$(ppm): 1.09(t,3H), 1.34(s,6H), 2.46 (q,2H), 3.36(s,2H), 4.37(s,2H), 4.93 (s,1H), 5.17(s,1H), |

TABLE 1-continued

| Compound No. | Substituents in General Formula [I] | | | | Etherification Process | Yield (%) | Physical Property Values |
|---|---|---|---|---|---|---|---|
| | Ar | R | Y | B | | | |
| | | | | | | | 6.7-7.3(m,13H) |
| 111 | CH₃CH=C(CH₃)-C₆H₄- | CH₃— | —O— | -C₆H₄-O-C₆H₅ | B | 76 | $C_{27}H_{30}O_2$ Calculated Found (%) (%) C: 83.90 84.07 H: 7.82 7.95 δCCl₄(ppm): 1.34(s,6H), 1.77(d,3H), 1.97 (s,3H), 3.36(s,2H), 4.37(s,2H), 5.71 (q,1H), 6.7-7.3(m,13H) |

Processes for preparing starting compounds of the general formulae [V], [VII] and [IX] will now be described in detail with reference to the following Synthesis Examples.

SYNTHESIS EXAMPLE 24

A compound of the following formula was synthesized according to the following procedures:

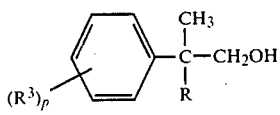

(1) A mixture of 10 g of an arylacetonitrile, 20 g of KOH, 20 g of H₂O and 2 g of triethylbenzyl ammonium bromide was maintained at 80° to 90° C. and methyl iodide in an amount of 1.2 moles per mole of the arylacetonitrile was added dropwise to the mixture over a period of 1 to 2 hours. Then, 10 g of KOH and 2 g of triethylbenzyl ammonium bromide were further added to the mixture. At the same temperature, a desired alkyl halide in an amount of 1.2 moles per mole of the arylacetonitrile was added dropwise to the mixture over a period of 1 to 4 hours.

The mixture was cooled to room temperature and was extracted with toluene. The intended dialkyl arylacetonitrile was obtained from the toluene extract.

(2) The dialkyl arylacetonitrile synthesized in (1) above was hydrolyzed at 130° to 150° C. with 50% H₂SO₄ or aqueous diethylene glycol/KOH to give a 2-aryl-2-alkylpropionic acid having the following formula:

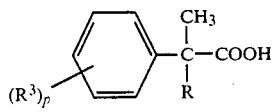

The properties of the typical compounds are shown below.

| $(R^3)_p$ | R | Melting Point (°C.) |
|---|---|---|
| H | CH₃— | 75-76.5 |
| 3-Cl | CH₃— | 66.5-67.5 |
| 3,4-Cl₂ | CH₃— | 93.5-94.5 |
| 4-CH₃ | CH₃— | 80-81.5 |
| 4-Cl | C₂H₅— | 59-61.5 |
| 4-OCH₃ | CH₃— | 82.5-84 |

(3) The 2-aryl-2-alkylpropionic acid synthesized in (2) above was reduced in tetrahydrofuran with lithium aluminum hydride to obtain the intended 2-aryl-2-alkylpropyl alcohol.

SYNTHESIS EXAMPLE 25

2-(4-Chlorophenyl)-2-methylpropyl alcohol was synthesized according to the following procedures.

(1) To 169 g of chlorobenzene was added 1.5 g of ferric chloride, and hydrogen chloride gas was blown into the mixture for 10 minutes. Then, 46 g of tert-butyl chloride was added dropwise to the mixture at 30° C. over a period of 1 hour. The mixture was maintained at 30° C. for 2 hours. The reaction mixture was washed with an aqueous solution of sodium carbonate and then with water, and evaporated under reduced pressure to give 25 g of 4-tert-butylchlorobenzene (bp.: 113° C./28 mmHg).

(2) To 25 g of 4-tert-butylchlorobenzene synthesized in (1) above were added 20 g of sulfuryl chloride and a catalytic amount of benzoyl peroxide, and the temperature was elevated and the mixture was maintained at 100° C. for 1 hour. Then, the mixture was distilled under reduced pressure to give 17.0 g of 2-(4-chlorophenyl)-2-methyl-1-chloropropane (bp.: 121°-123° C./10 mmHg).

(3) To 100 ml of dry tetrahydrofuran were added 2.7 g of magnesium (turnings) and a small amount of iodine as the catalyst, and 20.3 g of 2-(4-chlorophenyl)-2-methyl-1-chloropropane was added dropwise to the mixture under reflux over a period of 30 minutes. The mixture was further refluxed for 10 hours. Then, the mixture was cooled to room temperature and oxygen gas was blown into the mixture for 1 hour. Then, a saturated aqueous solution of ammonium chloride was added to the mixture and the majority of tetrahydrofuran was removed by distillation under reduced pressure. The residue was extracted with toluene, and the toluene extract was evaporated under reduced pressure to give a crude alcohol.

Recrystallization from cold hexane gave 13.3 g of 2-(4-chlorophenyl)-2-methylpropyl alcohol (mp.: 46°-48° C.).

Elementary Analysis Values as $C_{10}H_{13}ClO$: Calculated: C=65.04%, H=7.10%, Cl=19.20% Found: C=64.18%, H=6.95%, Cl=19.16%

SYNTHESIS EXAMPLE 26

2-(3,4-Methylenedioxyphenyl)-2-methylpropyl alcohol was synthesized according to the following procedures.

(1) Reaction was carried out as indicated by the following reaction formula:

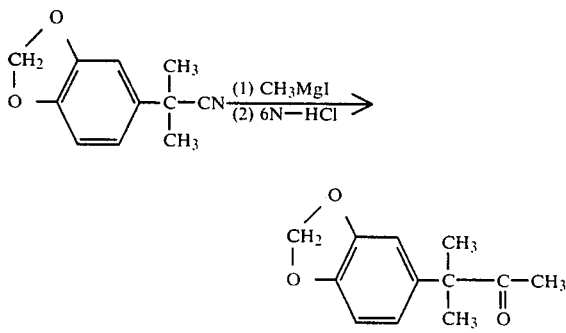

More specifically, 2.7 g of magnesium (turnings) and a small amount of iodine as the catalyst were added to 100 ml of dry ether, and 17 g of methyl iodide was gradually added dropwise to the mixture. Then, the mixture was refluxed for 30 minutes, and while the temperature was elevated, 100 ml of benzene was added to the mixture to substitute ether by benzene. Then, 18.9 g of the starting nitrile was added dropwise to the mixture under reflux.

The mixture was further refluxed for 3 hours, and then, 20 ml of 6N HCl was added dropwise to the mixture under cooling over a period of 30 minutes. Then, the temperature was elevated and the mixture was refluxed for 7 hours. Then, the mixture was cooled to room temperature, and the benzene layer was separated, washed with water, dried over $Na_2SO_4$, and evaporated under reduced pressure to give 19.2 g of 2-(3,4-methylenedioxyphenyl)-2-methyl-3-butanone.

$\nu_{max}^{film}$ (cm$^{-1}$): 2970, 2890, 1720, 1495, 1250, 1045, 940, 820, $\delta CCl_4$ (ppm): 1.38 (s, 6H), 1.85 (s, 3H), 5.91 (s, 2H), 6.67 (s, 3H).

(2) At a temperature lower than 20° C., 12.8 g of bromine was added dropwise to a mixture of 7.4 g of sodium hydroxide, 35 ml of water and 10 ml of dioxane. Then, the temperature was elevated and at 90° C., 10 g of 2-(3,4-methylenedioxyphenyl)-2-methyl-3-butanone was gradually added to the mixture, and the mixture was refluxed at 90° to 95° C. for 2 hours.

The mixture was cooled to room temperature, and a necessary amount of sodium hydrogensulfite was added to the mixture. Then, the mixture was extracted with toluene. The aqueous residual solution was made acidic with concentrated hydrochloric acid and extracted with toluene. The toluene extract was washed with water, dried over $Na_2SO_4$, and evaporated under reduced pressure to give 7.5 g of 2-(3,4-methylenedioxyphenyl)-2-methylpropionic acid.

$\delta CCl_4$ (ppm): 1.61 (s, 6H), 6.03 (s, 2H), 7.04 (s, 3H).

(3) In tetrahydrofuran, 2-(3,4-methylenedioxyphenyl)-2-methylpropionic acid was reduced with lithium aluminum hydride to give 2-(3,4-methylenedioxyphenyl)-2-methylpropyl alcohol.

$\nu_{max}^{film}$ (cm$^{-1}$): 3390, 2960, 1495, 1235, 1040, 940, 810.

$\delta CCl_4$ (ppm): 1.25 (s, 6H), 3.39 (s, 2H), 5.87 (s, 2H), 6.6–6.9 (m, 3H).

SYNTHESIS EXAMPLE 27

2-(4-Difluoromethoxyphenyl)-2-methylpropyl alcohol was synthesized according to the following procedures.

(1) In 100 ml of acetonitrile was dissolved 18.0 g of 2,4-bis(4-hydroxyphenyl)-4-methyl-2-pentene, and 10 g of 50% NaOH was added to the solution. Then, blowing of difluorochloromethane (Freon 22) was started at 60° to 70° C. When difluorochloromethane was blown in an amount of about 60% of the amount necessary for the reaction (about 20 minutes after initiation of blowing), 10 g of 50% KOH was further added to the reaction mixture and blowing was further continued. When difluorochloromethane was blown in an amount 1.5 times the amount necessary for the reaction, blowing was stopped. The reaction mixture was cooled to room temperature and poured into 500 ml of water, and the mixture was extracted with toluene. The toluene layer was washed with water, dried over $Na_2SO_4$, and evaporated under reduced pressure. The obtained crude ether was purified by column chromatography on 200 g of silica gel (toluene was used as eluent) to give 19.2 g of 2,4-bis(4-difluoromethoxyphenyl)-4-methyl-2-pentene. The yield was 77%.

$n_D^{20.4}$ 1.5285

(2) In 100 ml of acetone was dissolved 8.0 g of 2,4-bis(4-difluoromethoxyphenyl)-4-methyl-2-pentene, and 30 g of $KMnO_4$ was added to the solution at 30° C. The mixture was stirred at 30° C. for 10 hours, and 20 ml of ethyl alcohol was added dropwise to the mixture under cooling to decompose excessive $KMnO_4$. The mixture was stirred for 1 hour, and manganese dioxide formed by the reaction was removed by filtration and sufficiently washed with water and then with acetone. The filtrate was evaporated under reduced pressure, and a dilute solution of hydrochloric acid was added to the residue and the mixture was extracted with toluene. A dilute aqueous solution of NaOH was added to the toluene extract, and the mixture was sufficiently shaken and the aqueous solution layer was separated, was made acidic with concentrated hydrochloric acid and extracted with toluene. The toluene extract was washed with water, dried, and evaporated under reduced pressure to give 4.2 g of intended 2-(4-difluoromethoxyphenyl)-2-methylpropionic acid (mp.: 68.5°–69.5° C.). The yield was 84%.

$\delta CCl_4$ (ppm): 1.58 (s, 6H), 6.42 (t, 1H, J=7 5 Hz), 7.03 (d, 2H, JAB=8.8 Hz), 7.37 (d, 2H, JAB=8.8 Hz) (AB type), 11.76 (broad s, 1H)

(3) To a mixture of 20 ml of tetrahydrofuran and 0.5 g of lithium aluminum hydride was added dropwise a solution of 2.0 g of 2-(4-difluoromethoxyphenyl)-2-methylpropionic acid in 10 ml of tetrahydrofuran at 40° C. Then, the temperature was elevated, and the mixture was refluxed for 30 minutes.

The mixture was cooled to room temperature, and ethanol was added dropwise to the mixture to decompose excessive lithium aluminum hydride. Then, water was added to the mixture to complete the decomposition. The formed precipitate was removed by filtration, and tetrahydrofuran was removed from the filtrate by distillation under reduced pressure. The residue was extracted with benzene, and the benzene extract was washed with water, dried over $Na_2SO_4$, and evaporated under reduced pressure to give 1.8 g of 2-(4-difluoromethoxyphenyl)-2-methylpropyl alcohol. The yield was 96%.

$\nu_{max}^{film}$ (cm$^{-1}$): 3360, 1510, 1380, 1220, 1185, 1130, 1040, 835

SYNTHESIS EXAMPLE 28

2-(4-Fluorophenyl)-2-methylbutyl alcohol was synthesized according to the following procedures.

(1) A 300-ml flask was charged with 16.6 g of 4-fluorotoluene, 30.0 g of NBS, 0.5 g of benzoyl peroxide and 150 ml of carbon tetrachloride, and the mixture was refluxed for 2.0 hours. The reaction mixture was cooled to room temperature, and the formed precipitate was removed by filtration and the residual CCl$_4$ solution was washed with dilute alkali and then with water, dried over Na$_2$SO$_4$, and evaporated under reduced pressure to give 28.8 g of crude 4-fluorobenzyl bromide.

A solution of 28.8 g of the so obtained crude bromide in 30 ml of ethanol was added dropwise to a mixture of 8.8 g of NaCN and 9.0 g of water at 70° to 80° C. over a period of 30 minutes. The mixture was maintained at 80° C. for 5.0 hours, and the mixture was cooled to room temperature and poured into water. Then, celite and benzene were added to the mixture and the mixture was stirred, and celite was removed by filtration.

The benzene layer was separated, washed with water, dried over Na$_2$SO$_4$, and evaporated under reduced pressure to give 13.2 g of crude 4-fluorobenzyl cyanide.

$\nu_{max}^{film}$ (cm$^{-1}$): 2270, 1615, 1520, 1430, 1240, 1170, 825

(2) A flask was charged with 12.8 g of crude 4-fluorobenzyl cyanide, 40 g of 50% NaOH and 2 g of triethylbenzyl ammonium bromide, and while the mixture was stirred, 14 g of methyl iodide was added dropwise to the mixture at 70° C. over a period of 15 minutes.

The mixture was maintained at 70° C. for 30 minutes and was then cooled to room temperature. The mixture was poured into ice water. The mixture was extracted with benzene, and the benzene extract was washed with water, dried over Na$_2$SO$_4$, and evaporated under reduced pressure to give 13.4 g of α-methyl-4-fluorobenzyl cyanide.

A flask was charged with 7.0 g of α-methyl-4-fluorobenzyl cyanide, 15 g of KOH, 10 g of H$_2$O and 2.0 g of triethylbenzyl ammonium chloride, and 10 ml of ethyl bromide was added dropwise to the mixture under stirring at 80° C. over a period of 1 hour. The mixture was maintained at the same temperature for 2 hours. The subsequent operation was carried out in the same manner as described above to give 7.9 g of crude α-ethyl-α-methyl-4-fluorobenzyl cyanide.

7.6 g of crude α-ethyl-α-methyl-4-fluorobenzyl cyanide, 20 ml of H$_2$O and 20 ml of concentrated sulfuric acid were refluxed at 134° to 137° C. for 5.5 hours. The mixture was cooled to room temperature and extracted with benzene, and the benzene solution was extracted with dilute alkali and the obtained dilute alkali extract was adjusted to pH 7.5 with concentrated hydrochloric acid, and extracted with benzene to remove impurities. Then, the aqueous solution was adjusted to pH 4.6 with concentrated hydrochloric acid and extracted with benzene. The benzene extract was washed with water, dried over Na$_2$SO$_4$, and evaporated under reduced pressure to give 3.8 g of 2-(4-fluorophenyl)-2-methylbutyric acid.

$\delta$CDCl$_3$ (ppm): 0.85 (t, 3H, J=7 Hz), 1.55 (s, 3H), 1.8–2.3 (m, 2H), 7.0–7.6 (m, 4H), 11.3 (broad s, 1H).

(3) A solution of 3.0 g of 2-(4-fluorophenyl)-2-methylbutyric acid in 10 ml of tetrahydrofuran was added dropwise to a mixture of 20 ml of tetrahydrofuran and 0.5 g of lithium aluminum hydride at 40° C. The temperature was then elevated and the mixture was refluxed for 30 minutes. The mixture was cooled to room temperature and ethanol was added dropwise to the mixture to decompose excessive lithium aluminum hydride. Then, water was added to the mixture to complete the decomposition. The formed precipitate was removed by filtration and tetrahydrofuran was removed from the filtrate by distillation under reduced pressure. The residue was extracted with benzene, and the benzene extract was washed with water direct, over Na$_2$SO$_4$, and evaporated under reduced pressure to give 2.6 g of 2-(4-fluorophenyl)-2-methylbutyl alcohol.

$n_D^{23}$ 1.5035

$\nu_{max}^{film}$ (cm$^{-1}$): 3360, 1610, 1520, 1240, 1175, 1040, 840.

SYNTHESIS EXAMPLE 29

2-(4-Methylthiophenyl)-2-methylpropyl alcohol was synthesized according to the following procedures.

(1) Synthesis of 4-methylthiobenzyl chloride:

To 200 ml of 1,2-dichloroethane was added 18.2 g of methylal, and 61.5 g of anhydrous aluminum chloride was dissolved in the solution under cooling with water. Then, 24.8 g of thioanisole was added dropwise to the mixture at room temperature and the mixture was stirred for 3 hours to effect reaction. The reaction mixture was poured into water, and concentrated hydrochloric aicd was added to dissolve solids. Then, the mixture was extracted with benzene, and the extract was washed with water and with a dilute aqueous solution of sodium hydrogencarbonate and washed with water again. Then, the extract was dried over Na$_2$SO$_4$, and evaporated to give 30.7 g of an oily residue.

(2) Synthesis of (4-methylthiophenyl)-acetonitrile:

In 12 g of water was dissolved 10.5 g of sodium cyanide, and the solution was heated at 60° C. A solution of 30.7 g of the oily product obtained in (1) above in 35 ml of ethanol was added dropwise to the above solution and the mixture was refluxed for 4 hours to effect reaction. The reaction mixture was post-treated according to conventional procedures and purified by column chromatography using benzene as eluent to give 14.7 g of (4-methylthiophenyl)-acetonitrile (oily product).

$\nu_{max}^{film}$ (cm$^{-1}$): 2260, 1500, 1420, 1105, 800.

$\delta$CCl$_4$ (ppm): 2.37 (s, 3H), 3.56 (s, 2H), 7.16 (s, 4H)

(3) Synthesis of 1-(4-methylthiophenyl)-1,1-dimethylacetonitrile:

In the same manner as described in Synthesis Example 24-(1), 13.9 g of the intended product was prepared from 13.1 g of (4-methylthiophenyl)acetonitrile. $\delta$CCl$_4$ (ppm): 1.66 (s, 6H), 2.45 (s, 3H), 7.2–7.6 (m, 4H)

(4) Synthesis of 1-(4-methylthiophenyl)-1-methylpropionic acid:

To a mixture of 5.0 g of potassium hydroxide, 5 g of water and 20 ml of diethylene glycol was added 3.8 g of 1-(4-methylthiophenyl)-1,1-dimethylacetonitrile, and reaction was carried out at 130° to 140° C. for 7 hours. The reaction mixture was cooled and poured into water. The mixture was extracted with benzene and the aqueous residual solution was made acidic with concentrated hydrochloric acid, on that occasion precipitation was caused. The mixture was extracted with ether, and the extract was washed with a saturated aqueous solution of sodium chloride, dried over Na$_2$SO$_4$, and evaporated to give 1.9 g of solid 1-(4-methylthiophenyl)-1-methylpropionic acid.

δ acetone-$d_6$ (ppm): 1.54 (s, 6H), 2.43 (s, 3H), 7.0–7.5 (m, 4H).

(5) Synthesis of 2-(4-methylthiophenyl)-1-methylpropyl alcohol:

According to conventional procedures, 1.9 g of 1-(4-methylthiophenyl)-1-methylpropionic acid was reduced with lithium aluminum hydride to give 1.5 g of the desired alcohol.

$\delta CCl_4$ (ppm): 1.26 (s, 6H), 2.39 (s, 3H), 3.38 (s, 2H), 7.0–7.4 (m, 4H).

SYNTHESIS EXAMPLE 30

2-(4-Chlorophenyl)-2-methylpropylthiol was synthesized according to the following procedures.

(1) Synthesis of 2-(4-chlorophenyl)-2-methylpropyl tosylate:

To a mixture of 10.0 g of 2-(4-chlorophenyl)-2-methylpropyl alcohol and 20 ml of pyridine was added 10.8 g of p-toluene-sulfonyl chloride, and the mixture was reacted at 50° to 55° C. for 1 hour. The reaction mixture was poured into ice water, and the mixture was made acidic with dilute hydrochloric acid and extracted with benzene. The benzene extract was washed with a saturated aqueous solution of sodium chloride, dried over $Na_2SO_4$, and evaporated under reduced pressure to give 19.3 g of a white solid residue (mp: 69°–71.5° C.).

$\nu_{max}^{KBr}$ (cm$^{-1}$): 1595, 1480, 1355, 1175, 970, 825

$\delta CCl_4$ (ppm): 1.31 (s, 6H), 2.44 (s, 3H), 3.89 (s, 2H), 7.13 (s, 4H), 7.18–7.60 [m, 4H (AB type)]

(2) Synthesis of bis[2-(4-chlorophenyl)-2-methylpropyl]-disulfide:

A mixture of 13.0 g of the tosylate obtained in (1) above, 20.0 g of sodium hydrosulfide (70% purity) and 100 ml of 90% ethanol was stirred and refluxed for 3 hours to effect reaction. The reaction mixture was poured into water, and the mixture was extracted with benzene and the benzene extract was washed with water and dried over $Na_2SO_4$, and evaporated under reduced pressure to give 7.9 g of an oily residue. The oily residue was purified by silica gel column chromatography using a 1:3 mixed solvent of benzene and hexane as diluent to give 5.3 g of the desired product (oily product).

$\nu_{max}^{film}$ (cm$^{-1}$): 2950, 1500, 1410, 1395, 1380, 1120, 1105, 1020, 830, 755.

$\delta CCl_4$ (ppm): 1.31 (s, 6H), 2.81 (s, 2H), 7.18 (d, 4H)

Elementary Analysis Values as $C_{20}H_{24}Cl_2S_2$; Calculated: C=60.17%, H=6.01%, S=16.06%, Cl=17.76% Found: C=59.06%, H=6.07%, S=16.55%, Cl=17.56%

(3) Synthesis of 2-(4-chlorophenyl)-2-methylpropylthiol:

In 25 ml of dry ether was suspended 0.095 g of lithium aluminum hydride, and a solution of 1.0 g of bis[2-(4-chlorophenyl)-2-methylpropyl]disulfide in 10 ml of ether was added dropwise to the suspension, and the mixture was refluxed for 2 hours. The reaction mixture was poured into water and 15% dilute sulfuric acid was added, and the mixture was extracted with benzene. The benzene extract was washed with a saturated aqueous solution of sodium chloride, dried over $Na_2SO_4$, and evaporated under reduced pressure to give 1.0 g of an oily residue.

$\nu_{max}^{film}$ (cm$^{-1}$): 2965, 2570, 1495, 1405, 1390, 1370, 1105, 1020, 830.

$\delta CCl_4$ (ppm): 0.80 (t, 1H), 1.33 (s, 6H), 2.68 (d, 2H), 7.23 (s, 4H).

Insect pests to which the insecticidal and acaricidal composition of the present invention can be applied are described below.

[Scientific name—Common name]

1. Hemiptera:

*Nephotettix cincticeps* Uhler-Green rice leafhopper
*Sogata furcifera* Horvath-White-backed planthopper
*Nilaparvata lugens* Stal-Brown planthopper
*Delphacodes striatella* Fallén-Small brown planthopper
*Eurydema rugosum* Motschulsky-Cabbage bug
*Eysarcoris parvus* Uhler-Whitespotted spined bug
*Halyomorpha mista* Uhler-Brown-marmorated stink bug
*Lagynotomus elongatus* Dallas-Rice stink bug
*Nezara viridula* Linné-Southern green stink bug
*Cletus trigonus* Thunberg-Slender rice bug
*Stephanitis nashi* Esaki et Takeya-Japanese pear lace bug
*Stephanitis pyrioides* Scott-Azalea lace bug
*Psylla pyrisuga* Föster-Pear sucker
*Psylla mari* Schmidberger-Apple sucker
*Aleurolobus taonabae* Kuwana-Grape whitefly
*Dialeurodes citri* Ashmead-Citrus whitefly
*Trialeurodes vaporariorum* Westwood-Greenhouse whitefly
*Aphis gossypii* Glover-Cotton aphid
*Brevicornye brassicase* Linné-Cabbage aphid
*Myzus persicae* Sulzer-Green peach aphid
*Rhopalosiphum maidis* Fitch-Corn leaf aphid
*Icerya purchasi* Maskell-Cottonycushion scale
*Planococcus citri* Risso-Citrus mealybug
*Unaspis yanonensis* Kuwana-Arrowhead scale 2. Lepidoptera:

*Canephora asiatica* Staudinger-Mulberry bagworm
*acrocercops astaurota* Meyrick-Pear bark miner
*Lithocolletis ringoniella* Matsumura-Apple leaf miner
*Plutella maculipennis* Curtis-Diamond back moth
*Promalactis inopisema* Butler-Cotton seed worm
*Adoxophyes orana* Fischer von Röslerstamm-Smaller tea tortrix
*Bactra honesta* Meyrick-Mat rush worm
*Grapholitha glycinivorella* Matsumura-Soybean pod borer
*Cnaphalocrocis medinalis* Guenée-Grass leaf roller
*Etiella zinckenella* Treitschke-Lima-bean pod borer
*Ostrinia furnacalis* Hübner-European corn borer
*Syllepta derogata* Fabricius-Cotton leaf roller
*Hyphantria cunea* Drury-Fall webworm
*Trimeresia miranda* Butler-Magpie moth
*Lymantria dispar* Linné-Gypsy moth
*Phalera flavescens* Bremer et Grey-Black-marked prominent
*Agrotis fucosa* Butler-Common cutworm
*Heliothis obsoleta* Fablicius-Cotton boll worm
*Leucania separata* Walker-Armyworm
*Mamestera brassicae* Linné-Cabagge armyworm
*Plusia nigrisigna* Walker-Beetworm
*Spodoptera litura* Fablicius-Tobacco cutworm
*Parnara guttata* Bremer et Grey-Rice-plant skipper
*Pieris rapae* crucivora Boisduval-Common cabbageworm
*Chilo suppressalis* Walker-Rice stem borer 3. Coleoptera:

*Melanotus caudex* Candéze-Sweetpotato wireworm

*Anthrenus verbasci* Linné-Varied carpet beetle
*Tenebroides mauritanicus* Linné-Cadelle
*Lyctus brunneus* Stephens-Lyctus powder-post beetle
*Epilachna vigintioctomaculata* Fablicius-28-Spotted lady beetle
*Monochamus alternatus* Waterhouse-Japanese pine sawyer
*Xylotrechus pyrrhoderus* Bates-Grape borer
*Aulacophora femoralis* Motschulsky-Cucurbit leaf beetle
*Oulema oryzae* Kuwayama-Rice leaf beetle
*Phyllotreta striolata* Fablicius-Striped flea beetle
*Callosobruchus chinensis* Linné-Azuki bean weevil
*Echinocnemis squameus* Billberg-Rice plant weevil
*Sitophilus oryzae* Linné-Small rice weevil
*Apoderus erythrogaster* Vollenhoven-Small black leaf-cut weevil
*Rhynchites heros* Roelofs-Peach curculio
*Anomala cuprea* Hope-Cupreous chafer
*Popillia japonica* Newman-Japanese beetle
4. Hymenoptera:
*Athalia rosae japonica* Rohwer-Cabbage sawfly
*Arge similis* Vollenhoven-Azalea sawfly
*Arge pagana* Panzer-Rose arge
5. Diptera:
*Tipula aino* Alexander-Rice crane fly
*Culex pipiens fatigans* Wiedemann-House mosquito
*Aedes aegypti* Linné-Yellow-fever mosquito
*Asphondylia* sp.-Soybean pod gall midge
*Hylemya antiqua* Meigen-Onion maggot
*Hylemya platura* Meigen-Seed corn maggot
*Musca domestica vicina* Macquart-House fly
*Dacus cucurbitae* Coquillett-Melon fly
*Chlorops oryzae* Matsumura-Rice stem maggot
*Agromyza oryzae* Munakata-Rice leaf miner
6. Siphonaptera:
*Pulex irritans* Linné-Human flea
*Xenopsylla cheopis* Rothschild-Tropical rat flea
*Ctenocephalides canis* Curtis-Dog flea
7. Thysanoptera:
*Scirtothrips dorsalis* Hood-Yellow tea thrips
*Thrips tabaci* Lindeman-Onion thrips
*Chloethrips oryzae* Williams-Rice thrips
8. Anoplura:
*Pediculus humanus corporis* De Geer-Body louse
*Phthirus pubis* Linné-Crab louse
*Haematopinus eurysternus* Nitzsh-Short-nosed cattle louse
9. Psocoptera:
*Trogium pulsatorium* Linné-Flour booklice
*Liposcelis bostrychophilus* Badonnel-Flattened booklice
10. Orthoptera:
*Gryllotalpa africana* palisot de Beauvois-African mole cricket
*Locusta migratoria danica* Linné-Asiatic locust
*Oxya japonica* Willemse-Short-Winged rice grass hopper
11. Dictyoptera:
*Blattella germanica* Linné-German cockroach
*Periplaneta fuliginosa* Serville-Smokybrown cockroach
12. Acarina:
*Boophilus microplus* Canestrini-Bull tick
*Hemitarsonemus latus* Banks-Broad mite
*Panonychus citri* McGregor-Citrus red mite
*Tetranychus telarius* Linné-Carmine mite
*Tetranychus urticae* Koch-Two-spotted spider mite
*Rhizoglyphus echinophus* Fumouze et Robin-Bulb mite When the compound of the present invention is actually applied, it may be used singly without incorporation of other components. Ordinarily, however, in order to facilitate the application, the compound of the present invention is mixed with a carrier to prepare an appropriate formulation and this formulation is diluted according to need before the application. No particular condition is necessary for preparing a formulation of the compound of the present invention but according to methods known to those skilled in the art of manufacture of agricultural chemicals, the compound of the present invention may optionally be prepared into any of various formulations such as emulsifiable concentrates, wettable powders, dusts, granules, fine granules, oils, aerosols, heating fumigants (mosquito coil and electric incenses), smoking agents such as fogging agents, non-heating fumigants and poisonous diets. These formulations may be applied to various uses according to intended objects.

Furthermore, it is possible to obtain an enhanced insecticidal and acaricidal effect by using two or more of the compounds of the present invention in combination. Moreover, multi-purpose compositions having excellent activities can be obtained by combining the compounds of the present invention with other physiologically active substances, for example, allethrin, N-(chrysanthemoylmethyl)-3,4,5,6-tetrahydrophthalimide, 5-benzyl-3-furylmethyl chrysanthemate, 3-phenoxybenzyl chrysanthemate, 5-propargylfurfuryl chrysanthemate, other known cyclopropanecarboxylic acid esters, such as 3-phenoxybenzyl 3-(2,2-dichlorovinyl)-2,2-dimethyl-cyclopropane-1-carboxylate, 3-phenoxy-α-cyano-benzyl 3-(2,2-dichlorovinyl)-2,2-dimethyl-cyclopropane-1-carboxylate, 3-phenoxy-α-cyano-benzyl 3-(2,2-dibromovinyl)-2,2-dimethyl-cyclopropane-1-carboxylate, other synthetic pyrethroids such as 3-phenoxy-α-cyanobenzyl α-isopropyl-4-chlorophenylacetate and isomers thereof, pyrethrum extracts, organosphosphorous insecticides such as O,O-diethyl-O-(3-oxo-2-phenyl-2H-pyridazin-6-yl)-phosphorothioate (supplied under registered tradename "Ofunack" by Mitsuitoatsu Chemicals, Inc.), O,O-dimethyl-O-(2,2-dichlorovinyl)phosphate (DDVP), O,O-dimethyl-O-(3-methyl-4-nitrophenyl)phosphorothioate, diazinon, O,O-dimethyl-O-4-cyanophenylphosphorothioate, O,O-dimethyl-S-[α-(ethoxycarbonyl)benzyl]phosphorodithioate, 2-methoxy-4H-1,3,2-benzodioxaphosphorin-2-sulfide and O-ethyl-O-4-cyanophenyl phenyl phosphonothioate, carbamate insecticides such as 1-naphthyl-N-methylcarbamate (NAC), m-tolyl-N-methylcarbamate (MTMC), 2-dimethylamino-5,6-dimethylpyrimidin-4-yl-dimethylcarbamate (Pyrimer), 3,4-dimethylphenyl N-methylcarbamate and 2-isopropoxyphenyl N-methylcarbamate, other insecticides, acaricides, fungicides, nematocides, herbicides, plant growth regulators, fertilizers, BT agents, insect hormones and other agricultural chemicals. Furthermore, synergistic effects are expected by combining the compounds of the present invention with these physiologically active substances.

Furthermore, the effects of the compounds of the present invention can be multiplied by combining the compounds of the present invention with synergists for pyrethroids, such as α-[2-(2-butoxyethoxy)ethoxy]-4,5-methylenedioxy-2-propyltoluene (piperonyl butoxide), 1,2-methylenedioxy-4-[2-(octylsulfinyl)propyl]benzene (Sulfoxide), 4-(3,4-methylenedioxyphenyl)-5-methyl- 1,3-dioxane (Safroxane), N-(2-ethylhexyl)-bicylo(2,2,1)-hepta-5-ene-2,3-dicarboxyimide (MGK-264), octachlorodipropyl ether (S-421) and isobornyl thiocyanoacetate (Sarnite).

Though the compounds of the present invention are highly stable against light, heat and oxidation, compositions having much stabilized activities can be obtained by mixing the compounds of the present invention with appropriate amounts of antioxidants or ultraviolet absorbents, for example, phenol derivatives such as BHT and BHA, bisphenol derivatives, arylamines such as phenyl-α-naphthylamine, phenyl-β-naphthylamine and phenetidine, acetone condensates thereof and benzophenone type compounds, as stabilizers according to need.

In the insecticidal and acaricidal composition of the present invention, the above-mentioned 2-arylpropyl ether or thioether derivative is incorporated in an amount of 0.001 to 95% by weight, preferably 0.01 to 50% by weight.

The insecticidal and acaricidal composition of the present invention will now be described in detail with reference to the following Formulation Examples that by no means limit the scope of the present invention.

Incidentally, all of "parts" given hereinafter are by weight, and the compounds of the present invention are designated by compound numbers shown in Table 1.

FORMULATION EXAMPLE 1

A mixture of 20 parts of a compound selected from the compounds Nos. 1 through 111 shown in Table 1 (hereinafter referred to as "the compound of the present invention"), 20 parts of Sorpol (registered Trademark for the product supplied by Toho Chemical Industrial Co., Ltd.) and 60 parts of xylol was stirred to give an emulsifiable concentrate.

FORMULATION EXAMPLE 2

In 10 parts of acetone was dissolved 1 part of the compound of the present invention, and 99 parts of clay for dusts was added to the solution and the mixture was evaporated to give a dust.

FORMULATION EXAMPLE 3

To 20 parts of the compound of the present invention was added 5 parts of a surface active agent, and the mixture was sufficiently blended and 75 parts of diatomaceous earth was added thereto. The mixture was blended in a crusher to give a wettable powder.

FORMULATION EXAMPLE 4

To 0.2 part of the compound of the present invention was added 2 parts of m-tolyl-N-methylcarbamate and 0.2 part of PAP (trademark for the property modifier supplied by Nippon Chemical Industrial Co., Ltd.) was further added. The mixture was dissolved in 10 parts of acetone and 97.6 parts of clay for dusts was added to the solution. The mixture was blended in a crusher and acetone was evaporated to give a dust.

FORMULATION EXAMPLE 5

To 0.2 part of the compound of the present invention was added 2 parts of Ofunack (Trademark for the product supplied by Mitsuitoatsu Chemicals, Inc.), and 0.2 part of PAP (described above) was further added. The mixture was dissolved in 10 parts of acetone and 97.6 parts of clay for dusts was added to the solution. The mixture was blended in a crusher and evaporated to give a dust.

FORMULATION EXAMPLE 6

To 0.1 part of the compound of the present invention was added 0.5 part of piperonyl butoxide, and the mixture was dissolved in kerosene so that the total amount was 100 parts, to give an oil solution.

FORMULATION EXAMPLE 7

To a mixture of 0.5 part of the compound of the present invention and 5 parts of Ofunack (described above) was added 5 parts of Sorpol SM-200 (described above), and the mixture was dissolved in 89.5 parts of xylol to give an emulsifiable concentrate.

FORMULATION EXAMPLE 8

A solution formed by mixing 0.4 part of the compound of the present invention and 2.0 parts of piperonyl butoxide with 6 parts of xylol and 7.6 parts of deodorized kerosene was charged in an aerosol vessel, and a valve portion was attached to the vessel and 84 parts of a propellant (liquefied petroleum gas) was fed under pressure through the valve portion to give an aerosol.

FORMULATION EXAMPLE 9

In an appropriate amount of chloroform was dissolved 0.05 g of the compound of the present invention, and the solution was uniformly adsorbed on the surface of an asbestos sheet having a size of 2.5 cm×1.5 cm×0.3 mm (thickness) to form a heating insecticidal fumigant to be placed on a hot plate.

FORMULATION EXAMPLE 10

In 20 ml of methanol was dissolved 0.5 g of the compound of the present invention, and the solution was homogeneously mixed with stirring with 99.5 g of an incense carrier (3:5:1 mixture of tub powder, pyrethrum marc powder and wood flour). Methanol was evaporated and 150 ml of water was added. The mixture was sufficiently kneaded and the kneaded mixture was molded and dried to give a mosquito coil.

FORMULATION EXAMPLE 11

To a mixture of 1 part of the compound of the present invention, 3 parts of Ofunack (described above), 2 parts of Serogen 7A (Trademark for the product supplied by Daiichi Kogyo Seiyaku) and 2 parts of Sunekisu (supplied by Sanyo Kokusaku Pulp) was added 92 parts of clay, and an appropriate amount of water was added and the mixture was granulated and sieved to give a granule.

When the compound of the present invention is actually applied, it is ordinarily applied at a rate of 1 to 300 g, preferably 2 to 100 g, especially preferably 5 to 20 g, as the active ingredient per 10 ares.

In order to demonstrate that the compounds of the present invention have excellent insecticidal and acaricidal activities and they have very low toxicity to warm-blooded animals and fish, the results of Tests will now be described. Samples:

To a mixture of 20 parts of the compound of the present invention and 20 parts of Sorpol SM-200 (registered tradename for the product supplied by Toho Chemical Industrial Co., Ltd.) was added 60 parts of xylol, and the mixture was sufficiently blended. The obtained emulsifiable concentrate was diluted at a predetermined concentration with distilled water, and the obtained dilution was used.

In the fish toxicity test, the test compound was dissolved in acetone to form a 1% solution, and a predetermined amount of the solution was used.

Compounds (a) through (i) described below were tested as comparative compounds in the same manner as the compounds of the present invention.

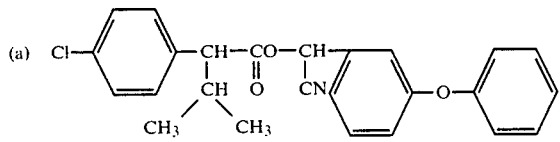

(a)

This compound is known from Japan Pesticide information, No. 33, 13 (1977).

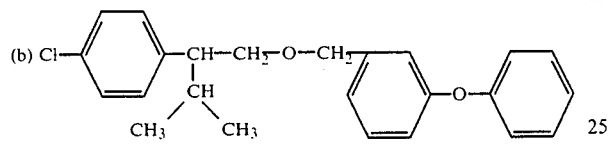

(b)

This compound is known from the specification of U.S. Pat. No. 4,073,812.

(c) Pyrethrin
(d) Ofunack (described above)
(e) MTMC (described above)
(f) Methomyl [S-methyl N-(methylcarbamoyloxy)thioacetoamidate]
(g) DDVP (described above)
(h) Orthorane (O,S-dimethyl N-acetylphosphoroamidothiolate)
(i) Permethrin Test 1 (Effect on Tobacco Cutworm)

An emulsifiable concentrate of a test compound prepared according to the method described in Formulation Example 1 was diluted to a concentration of 100 or 20 ppm. Sweet-potato leaves were immersed in the dilution for 10 seconds, air-dried and placed in a plastic cup having a diameter of 10 cm. Then second-instar larvae of tobacco cutworm were set free in the cup. The cup was allowed to stand still in a thermostat chamber maintained at 25° C. After 24 hours, the numbers of killed and living larvae were counted and the mortality was calculated. The obtained result was expressed by an average value obtained from the mortality calculated in three test cups.

The compounds of the present invention are designated by the compound numbers shown in Table 1.

The obtained results are shown in Table 2.

TABLE 2

| Test Compound | Mortality (%) 100 ppm | 20 ppm |
|---|---|---|
| Compound 2 | 100 | 90 |
| Compound 3 | 100 | 83 |
| Compound 4 | 100 | 95 |
| Compound 6 | 100 | 100 |
| Compound 7 | 100 | 80 |
| Compound 9 | 100 | 90 |
| Compound 11 | 100 | 100 |
| Compound 14 | 100 | 100 |
| Compound 17 | 100 | 80 |
| Compound 18 | 100 | 100 |
| Compound 20 | 100 | 100 |

TABLE 2-continued

| Test Compound | Mortality (%) 100 ppm | 20 ppm |
|---|---|---|
| Compound 23 | 100 | 80 |
| Compound 30 | 100 | 80 |
| Compound 33 | 100 | 90 |
| Compound 37 | 100 | 100 |
| Compound 39 | 100 | 90 |
| Compound 43 | 100 | 85 |
| Compound 45 | 100 | 100 |
| Compound 46 | 100 | 100 |
| Compound 47 | 100 | 90 |
| Compound 48 | 100 | 80 |
| Compound 49 | 100 | 100 |
| Compound 50 | 100 | 100 |
| Compound 51 | 100 | 100 |
| Compound 54 | 100 | 100 |
| Compound 55 | 100 | 100 |
| Compound 57 | 100 | 100 |
| Compound 58 | 100 | 100 |
| Compound 60 | 100 | 80 |
| Compound 62 | 100 | 80 |
| Compound 65 | 100 | 90 |
| Compound 66 | 100 | 100 |
| Compound 67 | 100 | 90 |
| Compound 70 | 100 | 90 |
| Compound 73 | 100 | 100 |
| Compound 74 | 100 | 100 |
| Compound 75 | 100 | 80 |
| Compound 76 | 100 | 90 |
| Compound 78 | 100 | 100 |
| Compound 81 | 100 | 90 |
| Compound 83 | 100 | 100 |
| Compound 85 | 100 | 80 |
| Compound 90 | 100 | 100 |
| Compound 92 | 100 | 90 |
| Compound 93 | 100 | 100 |
| Compound 94 | 100 | 100 |
| Compound 95 | 100 | 100 |
| Compound 97 | 100 | 100 |
| Compound 98 | 100 | 100 |
| Compound 99 | 100 | 100 |
| Compound 100 | 100 | 80 |
| Compound 101 | 100 | 100 |
| Compound 103 | 100 | 100 |
| Compound 108 | 100 | 100 |
| Comparative Compound (b) | 50 | 0 |
| Comparative Compound (f) | 100 | 80 |
| Comparative Compound (h) | 70 | 30 |

Test 2 (Tobacco Cutworm Larva Dipping Test)

A dilution having a chemical concentration of 100 or 20 ppm was prepared in the same manner as described in Test 1.

Second-instar and fifth-instar larvae of tobacco cutworm were dipped in the dilution for 5 seconds, and the excessive dilution was removed by a filter paper. Then, the larvae were set free in a plastic cup and an artificial diet was supplied thereto. The cup was allowed to stand still in a thermostat chamber maintained at 25° C. After 24 hours, the numbers of the killed and living larvae were counted and the mortality was calculated. The test was made on three cups and the result was expressed by an average value.

The obtained results are shown in Table 3.

TABLE 3

| Test Compound | Motality (%) Second-Instar Larvae 100 ppm | 20 ppm | Fifth-Instar Larvae 100 ppm | 20 ppm |
|---|---|---|---|---|
| Compound 3 | 90 | 70 | 70 | 60 |
| Compound 4 | 90 | 90 | 80 | 70 |
| Compound 6 | 100 | 100 | 100 | 100 |
| Compound 7 | 100 | 60 | 100 | 50 |
| Compound 11 | 100 | 90 | 100 | 70 |

TABLE 3-continued

| | Motality (%) | | | |
|---|---|---|---|---|
| | Second-Instar Larvae | | Fifth-Instar Larvae | |
| Test Compound | 100 ppm | 20 ppm | 100 ppm | 20 ppm |
| Compound 18 | 100 | 100 | 100 | 100 |
| Compound 20 | 100 | 90 | 100 | 80 |
| Compound 46 | 90 | 80 | 80 | 60 |
| Compound 48 | 90 | 70 | 70 | 60 |
| Compound 49 | 100 | 100 | 100 | 100 |
| Compound 50 | 100 | 100 | 100 | 90 |
| Compound 55 | 100 | 100 | 100 | 100 |
| Compound 59 | 100 | 100 | 100 | 100 |
| Compound 67 | 100 | 100 | 100 | 100 |
| Compound 74 | 100 | 70 | 80 | 50 |
| Compound 79 | 100 | 80 | 90 | 50 |
| Compound 90 | 100 | 100 | 100 | 90 |
| Compound 101 | 100 | 100 | 100 | 100 |
| Comparative Compound (b) | 0 | 0 | 0 | 0 |
| Comparative Compound (f) | 100 | 30 | 80 | 0 |
| Comparative Compound (g) | 50 | 20 | 30 | 10 |

Test 3 (Effect on Resistant Green Rice Leafhopper and Sensitive Green Rice Leafhopper)

Seedlings (having 2 to 3 leaves) of paddy rice were hydroponically cultured in a pot having a diameter of 5 cm. A chemical dilution having a concentration of 100 or 20 ppm, prepared in the same manner as described in Test 1, was applied with a sprayer at a rate of 3 ml per pot. The treated seedlings were air-dried and covered with a metal net cylinder, and female adults of resistant green rice leafhopper (collected at Nakagawara) and sensitive green rice leafhopper (collected at Chigasaki) were set, respectively, free in the pot at a density of 10 adults per pot. After 24 hours, the numbers of killed and living adults were counted and the mortality was calculated. The test was made on three pots and the average value was calculated.

The obtained results are shown in Table 4.

TABLE 4

| | Mortality (%) | | | |
|---|---|---|---|---|
| | Green Rice Leafhopper Collected at Nakagawara | | Green Rice Leafhopper Collected at Chigasaki | |
| Test Compound | 100 ppm | 20 ppm | 100 ppm | 20 ppm |
| Compound 1 | 100 | 100 | 100 | 100 |
| Compound 2 | 100 | 95 | 100 | 80 |
| Compound 3 | 100 | 100 | 100 | 100 |
| Compound 4 | 100 | 70 | 100 | 50 |
| Compound 5 | 100 | 100 | 100 | 100 |
| Compound 6 | 100 | 100 | 100 | 100 |
| Compound 7 | 100 | 100 | 100 | 90 |
| Compound 9 | 100 | 90 | 100 | 70 |
| Compound 10 | 100 | 100 | 100 | 100 |
| Compound 11 | 100 | 100 | 100 | 100 |
| Compound 13 | 100 | 70 | 100 | 50 |
| Compound 14 | 100 | 100 | 100 | 100 |
| Compound 15 | 100 | 90 | 100 | 70 |
| Compound 16 | 100 | 100 | 100 | 90 |
| Compound 17 | 100 | 100 | 100 | 100 |
| Compound 18 | 100 | 100 | 100 | 100 |
| Compound 19 | 100 | 100 | 100 | 90 |
| Compound 20 | 100 | 80 | 100 | 50 |
| Compound 21 | 100 | 85 | 100 | 60 |
| Compound 22 | 100 | 80 | 100 | 50 |
| Compound 24 | 100 | 70 | 100 | 40 |
| Compound 25 | 100 | 100 | 100 | 100 |
| Compound 26 | 100 | 85 | 100 | 60 |
| Compound 27 | 100 | 70 | 100 | 50 |
| Compound 28 | 100 | 90 | 100 | 75 |
| Compound 30 | 100 | 100 | 100 | 100 |
| Compound 31 | 100 | 100 | 100 | 100 |

TABLE 4-continued

| | Mortality (%) | | | |
|---|---|---|---|---|
| | Green Rice Leafhopper Collected at Nakagawara | | Green Rice Leafhopper Collected at Chigasaki | |
| Test Compound | 100 ppm | 20 ppm | 100 ppm | 20 ppm |
| Compound 32 | 100 | 100 | 100 | 100 |
| Compound 33 | 100 | 100 | 100 | 100 |
| Compound 34 | 100 | 100 | 100 | 90 |
| Compound 35 | 100 | 70 | 100 | 50 |
| Compound 36 | 100 | 90 | 95 | 70 |
| Compound 37 | 100 | 70 | 100 | 50 |
| Compound 38 | 100 | 95 | 100 | 80 |
| Compound 39 | 100 | 100 | 100 | 100 |
| Compound 40 | 100 | 70 | 100 | 50 |
| Compound 41 | 100 | 100 | 100 | 100 |
| Compound 42 | 100 | 100 | 100 | 95 |
| Compound 43 | 100 | 100 | 100 | 90 |
| Compound 44 | 100 | 95 | 100 | 80 |
| Compound 45 | 100 | 100 | 100 | 100 |
| Compound 46 | 100 | 80 | 100 | 65 |
| Compound 47 | 100 | 100 | 100 | 100 |
| Compound 48 | 100 | 100 | 100 | 100 |
| Compound 49 | 100 | 100 | 100 | 100 |
| Compound 50 | 100 | 90 | 100 | 80 |
| Compound 51 | 100 | 100 | 100 | 100 |
| Compound 52 | 100 | 90 | 100 | 90 |
| Compound 53 | 100 | 100 | 100 | 80 |
| Compound 55 | 100 | 100 | 100 | 100 |
| Compound 56 | 100 | 100 | 100 | 90 |
| Compound 57 | 100 | 100 | 100 | 100 |
| Compound 58 | 100 | 100 | 100 | 100 |
| Compound 59 | 100 | 100 | 100 | 100 |
| Compound 60 | 100 | 90 | 100 | 60 |
| Compound 61 | 100 | 100 | 100 | 100 |
| Compound 63 | 100 | 100 | 100 | 95 |
| Compound 65 | 100 | 100 | 100 | 100 |
| Compound 66 | 100 | 100 | 100 | 100 |
| Compound 68 | 100 | 100 | 100 | 100 |
| Compound 70 | 100 | 100 | 100 | 100 |
| Compound 71 | 100 | 100 | 100 | 100 |
| Compound 72 | 100 | 80 | 100 | 65 |
| Compound 77 | 100 | 85 | 100 | 70 |
| Compound 78 | 100 | 100 | 100 | 100 |
| Compound 82 | 100 | 100 | 100 | 80 |
| Compound 85 | 100 | 100 | 100 | 100 |
| Compound 88 | 100 | 80 | 100 | 60 |
| Compound 90 | 100 | 100 | 100 | 100 |
| Compound 91 | 100 | 100 | 100 | 100 |
| Compound 93 | 100 | 100 | 100 | 75 |
| Compound 94 | 100 | 100 | 100 | 100 |
| Compound 95 | 100 | 100 | 100 | 100 |
| Compound 96 | 100 | 90 | 100 | 60 |
| Compound 97 | 100 | 100 | 100 | 100 |
| Compound 100 | 100 | 95 | 100 | 80 |
| Compound 101 | 100 | 100 | 100 | 100 |
| Compound 103 | 100 | 100 | 100 | 100 |
| Compound 107 | 100 | 100 | 100 | 100 |
| Compound 108 | 100 | 100 | 100 | 95 |
| Compound 109 | 100 | 90 | 100 | 70 |
| Comparative Compound (c) | 0 | 0 | 0 | 0 |
| Comparative Compound (d) | 20 | 10 | 90 | 40 |
| Comparative Compound (e) | 0 | 0 | 80 | 20 |

Test 4 (Effect on Diamond Back Moth)

Cabbage leaves were spread in a plastic cup, and 10 third-instar larvae of diamond back moth were set free in the cup.

A chemical dilution having a concentration of 100 or 20 ppm, prepared in the same manner as described in Test 1, was applied from an applicator at a rate of 3 ml per cup.

After scattering of the chemical dilution, the cup was covered, and after 24 hours, the numbers of killed and living larvae were counted and the mortality was calculated. The test was made on three cups and the average value was calculated.

The obtained results are shown in Table 5.

TABLE 5

| Test Compound | Mortality (%) | |
|---|---|---|
| | 100 ppm | 20 ppm |
| Compound 2 | 100 | 100 |
| Compound 4 | 100 | 100 |
| Compound 6 | 100 | 100 |
| Compound 7 | 100 | 80 |
| Compound 9 | 100 | 95 |
| Compound 11 | 100 | 90 |
| Compound 14 | 100 | 100 |
| Compound 17 | 100 | 90 |
| Compound 18 | 100 | 100 |
| Compound 20 | 100 | 100 |
| Compound 30 | 100 | 70 |
| Compound 33 | 100 | 90 |
| Compound 37 | 100 | 100 |
| Compound 45 | 100 | 100 |
| Compound 46 | 100 | 100 |
| Compound 48 | 100 | 100 |
| Compound 49 | 100 | 100 |
| Compound 50 | 100 | 100 |
| Compound 52 | 100 | 90 |
| Compound 53 | 100 | 100 |
| Compound 55 | 100 | 100 |
| Compound 57 | 100 | 75 |
| Compound 59 | 100 | 85 |
| Compound 62 | 100 | 50 |
| Compound 64 | 100 | 70 |
| Compound 66 | 100 | 60 |
| Compound 67 | 100 | 90 |
| Compound 71 | 100 | 60 |
| Compound 73 | 100 | 90 |
| Compound 78 | 100 | 100 |
| Compound 84 | 100 | 60 |
| Compound 90 | 100 | 100 |
| Compound 94 | 100 | 80 |
| Compound 99 | 100 | 80 |
| Compound 101 | 100 | 100 |
| Compound 104 | 100 | 70 |
| Comparative Compound (b) | 30 | 10 |
| Comparative Compound (f) | 10 | 0 |
| Comparative Compound (g) | 60 | 0 |

Test 5 (Effect on Green Peach Aphid)

Seedlings (having 3 to 4 leaves) of an eggplant grown on a pot were inoculated with green peach aphids and the insects were allowed to grow. The number of the insects was counted. A chemical dilution having a concentration of 100 ppm, prepared in the same manner as described in Test 1, was applied with a spray gun at a rate of 10 ml per pot. Then, the pot was placed in a glass green house. After 24 hours, the number of living insects was counted and the mortality was calculated.

The test was made on three pots, and the average value was calculated. The obtained results are shown in Table 6. In Table 6, mark "A" indicates a mortality higher than 95%, mark "B" indicates a mortality of 80 to 95%, mark "C" indicates a mortality of 50 to 80%, and mark "D" indicates a mortality lower than 50%.

TABLE 6

| Test Compound | Insecticidal Activity |
|---|---|
| Compound 1 | B |
| Compound 3 | A |
| Compound 5 | A |
| Compound 6 | A |
| Compound 7 | A |
| Compound 8 | B |
| Compound 9 | A |

TABLE 6-continued

| Test Compound | Insecticidal Activity |
|---|---|
| Compound 11 | A |
| Compound 12 | B |
| Compound 14 | A |
| Compound 15 | B |
| Compound 18 | A |
| Compound 20 | A |
| Compound 24 | A |
| Compound 29 | B |
| Compound 39 | A |
| Compound 41 | A |
| Compound 48 | A |
| Compound 49 | A |
| Compound 50 | A |
| Compound 52 | A |
| Compound 53 | B |
| Compound 55 | A |
| Compound 57 | A |
| Compound 59 | A |
| Compound 62 | B |
| Compound 64 | A |
| Compound 69 | A |
| Compound 73 | A |
| Compound 78 | A |
| Compound 86 | B |
| Compound 93 | A |
| Compound 95 | A |
| Compound 96 | B |
| Compound 103 | A |
| Compound 105 | B |
| Comparative Compound (b) | D |
| Comparative Compound (g) | D |
| Comparative Compound (h) | B |

Test 6 (Effect on Two-Spotted Spider mite Adults)

A kidney bean leaf disc perforated with a cork borer (15 mm in diameter) was placed on water-impregnated absorbent cotton (2 cm×2 cm), and 10 adults of two-spotted spider mite were set free. A chemical dilution having a concentration of 100 ppm was applied with an applicator in an amount of 3 ml.

The leaf disc-placed absorbent cotton was placed in a thermostat chamber maintained at 25° C. After 24 hours, the number of killed adults was counted and the mortality was calculated. The test was made on three leaf discs and the average value was calculated.

The obtained results are shown in Table 7.

TABLE 7

| Test Compound | Mortality (%) |
|---|---|
| Compound 1 | 100 |
| Compound 5 | 100 |
| Compound 6 | 100 |
| Compound 7 | 100 |
| Compound 11 | 100 |
| Compound 16 | 90 |
| Compound 18 | 100 |
| Compound 20 | 100 |
| Compound 25 | 90 |
| Compound 33 | 95 |
| Compound 35 | 85 |
| Compound 41 | 100 |
| Compound 45 | 100 |
| Compound 46 | 95 |
| Compound 47 | 100 |
| Compound 48 | 100 |
| Compound 49 | 100 |
| Compound 50 | 100 |
| Compound 56 | 80 |
| Compound 57 | 90 |
| Compound 59 | 100 |
| Compound 64 | 100 |
| Compound 69 | 60 |

TABLE 7-continued

| Test Compound | Mortality (%) |
|---|---|
| Compound 82 | 90 |
| Compound 90 | 100 |
| Compound 98 | 100 |
| Compound 105 | 100 |
| Comparative Compound (b) | 20 |
| Comparative Compound (c) | 0 |
| Comparative Compound (d) | 40 |

Test 7 (Effect on German Cockroach)

The bottom face of a high Petri dish having a diameter of 9 cm and a height of 9 cm was treated with 50 or 10 mg/m² of a test compound and the dish was air-dried. In order to prevent the adults from escaping from the dish, the inner wall of the dish was treated with butter. Then, 10 male adults of German cockroach were set free in each dish, and the dish was placed in a thermostat chamber maintained at 25° C. After 24 hours, the number of agonized and killed adults was counted. The test was made on two dishes and the average value was calculated. The obtained results are shown in Table 8.

TABLE 8

| | Mortality (%) | |
|---|---|---|
| Test Compound | 50 mg/m² | 10 mg/m² |
| Compound 1 | 100 | 100 |
| Compound 5 | 100 | 80 |
| Compound 6 | 100 | 100 |
| Compound 7 | 100 | 100 |
| Compound 9 | 100 | 100 |
| Compound 11 | 100 | 100 |
| Compound 14 | 100 | 100 |
| Compound 17 | 100 | 100 |
| Compound 18 | 100 | 100 |
| Compound 22 | 100 | 90 |
| Compound 31 | 100 | 100 |
| Compound 38 | 100 | 90 |
| Compound 39 | 100 | 90 |
| Compound 41 | 100 | 100 |
| Compound 43 | 100 | 100 |
| Compound 45 | 100 | 100 |
| Compound 47 | 100 | 90 |
| Compound 48 | 100 | 100 |
| Compound 49 | 100 | 100 |
| Compound 50 | 100 | 100 |
| Compound 52 | 100 | 90 |
| Compound 55 | 100 | 100 |
| Compound 59 | 100 | 100 |
| Compound 61 | 100 | 70 |
| Compound 65 | 100 | 90 |
| Compound 67 | 100 | 100 |
| Compound 73 | 100 | 100 |
| Compound 74 | 100 | 100 |
| Compound 79 | 100 | 100 |
| Compound 90 | 100 | 90 |
| Compound 93 | 100 | 100 |
| Compound 104 | 100 | 90 |
| Compound 109 | 100 | 100 |
| Comparative Compound (d) | 100 | 50 |
| Comparative Compound (g) | 100 | 40 |

Test 8 (Fish Toxicity)

A water tank having a width of 60 cm, a length of 30 cm and a height of 40 cm was filled with water, and 10 yearling carps having a body length of about 5 cm were set free in the tank and adapted to the environment in the tank. A test compound was applied so that the concentration in water was 10, 1 or 0.1 ppm. After 48 hours, the numbers of killed and living carps were counted and the influences on the fishes were examined. The obtained results are shown in Table 9.

TABLE 9

| Test Compound | Fish Toxicity, $TLm_{48}$ (ppm)* |
|---|---|
| Compound 1 | above 10 |
| Compound 2 | above 1 |
| Compound 4 | above 10 |
| Compound 6 | above 10 |
| Compound 7 | above 10 |
| Compound 8 | above 10 |
| Compound 11 | 0.01–0.05 |
| Compound 12 | above 10 |
| Compound 13 | above 10 |
| Compound 15 | above 10 |
| Compound 19 | above 10 |
| Compound 20 | above 10 |
| Compound 21 | above 10 |
| Compound 22 | above 10 |
| Compound 23 | above 1 |
| Compound 24 | above 10 |
| Compound 29 | above 10 |
| Compound 30 | above 1 |
| Compound 31 | above 10 |
| Compound 33 | above 10 |
| Compound 35 | above 10 |
| Compound 37 | above 10 |
| Compound 41 | above 10 |
| Compound 45 | above 1 |
| Compound 46 | above 10 |
| Compound 47 | above 10 |
| Compound 48 | above 10 |
| Compound 49 | above 10 |
| Compound 50 | above 10 |
| Compound 51 | above 1 |
| Compound 52 | above 10 |
| Compound 53 | above 10 |
| Compound 55 | above 0.1 |
| Compound 62 | above 1 |
| Compound 69 | above 1 |
| Compound 73 | above 10 |
| Compound 105 | above 1 |
| Compound 107 | above 1 |
| Comparative Compound (a) | below 0.005 |
| Comparative Compound (i) | below 0.005 |

Note:
*the chemical concentration at which ½ of the test fishes were killed within 48 hours Test 9 (Toxicity Test)

A predetermined amount of a solution or suspension of a test compound in corn oil was orally administered to male mice having a body weight of 19 to 23 g (0.2 ml per 10 g of the body weight). After 7 days, the number of killed mice was counted and the influences on the mice were examined. The obtained results are shown in Table 10.

TABLE 10

| Test Compound | Acute Toxicity at Oral Administration, LD-50* (mg/Kg) |
|---|---|
| Compounds 1 through 111 | above 500 |
| Comparative Compound (a) | 260 |
| Comparative Compound (c) | 340 |
| Comparative Compound (e) | 220 |
| Comparative Compound (f) | 28 |

Note:
*the amount of the chemical killing ½ of the test animals

What is claimed is:

1. A process for the preparation of 2-arylpropyl ether or thioether derivatives represented by the following formula (I):

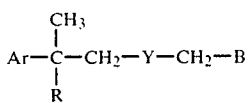
(I)

wherein Ar stands for an aryl group, R stands for a methyl or ethyl group, Y stands for an oxygen or sulfur atom, and B stands for a group represented by the following formula (II):

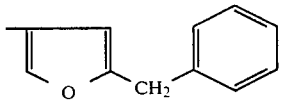
(II)

or the following formula (III):

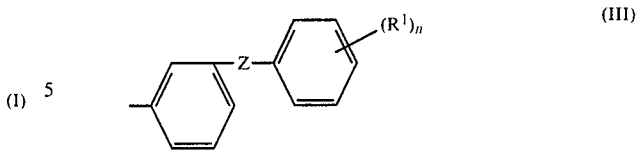
(III)

wherein Z stands for an oxygen or sulfur atom or a carbonyl or methylene group, $R^1$ stands for a hydrogen or halogen atom or a lower alkyl group or a lower alkoxy group, and n is an integer of from 1 to 5 with the proviso that when n is 2 or more, the group $R^1$ may be the same or different,
which comprises reacting a compound represented by the following formula (V):

(V)

with a compound represented by the following formula (VI):

(VI)

wherein Ar, R and B are defined above, A stands for a halogen atom and D is a group Y-H in which Y is as defined above, in the presence of a base in dimethylsulfoxide or sulfolone.

* * * * *